US009782756B2

(12) United States Patent
Ziemian et al.

(10) Patent No.: US 9,782,756 B2
(45) Date of Patent: Oct. 10, 2017

(54) PROCESS FOR THE PRODUCTION OF ETHYLENICALLY UNSATURATED CARBOXYLIC ACIDS OR ESTERS AND A CATALYST THEREFOR

(71) Applicant: Lucite International UK Limited, Southampton, Hampshire (GB)

(72) Inventors: Sabina Ziemian, Wilton (GB); Ian Andrew York, Wilton (GB)

(73) Assignee: Lucite International UK Limited, Southampton (GB)

( * ) Notice: Subject to any disclaimer, the term of this patent is extended or adjusted under 35 U.S.C. 154(b) by 0 days.

(21) Appl. No.: 15/099,854

(22) Filed: Apr. 15, 2016

(65) Prior Publication Data

US 2016/0228857 A1 Aug. 11, 2016

Related U.S. Application Data

(62) Division of application No. 13/883,863, filed as application No. PCT/GB2011/052147 on Nov. 4, 2011.

(30) Foreign Application Priority Data

Nov. 11, 2010 (GB) .................................. 1019092.4
Mar. 24, 2011 (GB) .................................. 1104977.2

(51) Int. Cl.
*B01J 27/18* (2006.01)
*C07C 67/343* (2006.01)
(Continued)

(52) U.S. Cl.
CPC ........... *B01J 27/1806* (2013.01); *B01J 23/04* (2013.01); *B01J 27/18* (2013.01); *B01J 27/182* (2013.01);
(Continued)

(58) Field of Classification Search
CPC ........ B01J 23/02; B01J 23/10; B01J 27/1806; B01J 27/18; B01J 27/182; B01J 35/00; B01J 35/002; B01J 35/02; B01J 35/026
(Continued)

(56) References Cited

U.S. PATENT DOCUMENTS

| 4,118,588 A | 10/1978 | Fouquet et al. |
| 4,324,908 A | 4/1982 | Grasselli et al. |

(Continued)

FOREIGN PATENT DOCUMENTS

| GB | 1573272 | 8/1980 | |
| JP | 07-196314 | * 8/1995 | ............. C01B 37/00 |

(Continued)

OTHER PUBLICATIONS

Monika Gupta, Rajive Gupta and Medha Anand, "Hydroxyapatite supported caesium carbonate as a new recyclable solid base catalyst for the Knoevenagel condensation in water", Beilstein Journal of Organic Chemistry, 2009, 5 No. 68 (7 pages).

(Continued)

*Primary Examiner* — Patricia L Hailey
(74) *Attorney, Agent, or Firm* — Shumaker, Loop & Kendrick, LLP

(57) ABSTRACT

A method of producing an ethylenically unsaturated carboxylic acid or ester such as (meth) acrylic acid or alkyl esters thereof, for example, methyl methacrylate is described. The process comprises the steps of contacting formaldehyde or a suitable source thereof with a carboxylic acid or ester, for example, propionic acid or alkyl esters thereof in the presence of a catalyst and optionally an alcohol. The catalyst comprises group II metal phosphate crystals having rod or needle like morphology or a suitable source thereof. The phosphate may be a hydroxyapatite, pyrophosphate, hydroxyphosphate, $PO_4^{2-}$ phosphate or mixtures thereof.

(Continued)

TEM Image of Example 1 Crystals

The group II metal may be selected from Ca, Sr, Ba or mixtures thereof, for example, strontium hydroxyapatite and calcium hydroxyapatite. A catalyst system comprising a crystalline metal phosphate catalyst and a catalyst support is also described. The metal phosphate has rod/needle like morphology.

14 Claims, 8 Drawing Sheets

(51) Int. Cl.
  $B01J\ 37/03$ (2006.01)
  $B01J\ 23/04$ (2006.01)
  $B01J\ 35/00$ (2006.01)
  $B01J\ 35/10$ (2006.01)
  $B01J\ 27/182$ (2006.01)
  $B01J\ 35/02$ (2006.01)
  $C07C\ 67/30$ (2006.01)
  $B01J\ 23/02$ (2006.01)
  $B01J\ 23/10$ (2006.01)

(52) U.S. Cl.
  CPC ............ $B01J\ 35/002$ (2013.01); $B01J\ 35/02$ (2013.01); $B01J\ 35/1009$ (2013.01); $B01J\ 35/1014$ (2013.01); $B01J\ 37/03$ (2013.01); $C07C\ 67/30$ (2013.01); $C07C\ 67/343$ (2013.01); $B01J\ 23/02$ (2013.01); $B01J\ 23/10$ (2013.01)

(58) Field of Classification Search
  USPC .......................................... 502/208; 423/308
  See application file for complete search history.

(56) References Cited

U.S. PATENT DOCUMENTS

| | | | |
|---|---|---|---|
| 4,560,790 A | 12/1985 | Ryu | |
| 6,323,383 B1* | 11/2001 | Tsuchida | B01J 27/1806 44/300 |
| 8,029,817 B2* | 10/2011 | Sayer | A61L 27/12 423/155 |
| 8,232,433 B2* | 7/2012 | Onda | C07C 29/34 502/340 |
| 9,211,529 B2* | 12/2015 | Fagan | B01J 27/182 |
| 2007/0232487 A1* | 10/2007 | Naganuma | B01D 53/885 502/208 |
| 2007/0255079 A1* | 11/2007 | Tsuchida | C07C 29/34 568/902.2 |
| 2010/0040668 A1* | 2/2010 | Riman | A61K 31/12 424/426 |
| 2012/0165577 A1* | 6/2012 | Fagan | B01J 27/1806 568/902.2 |
| 2013/0078476 A1* | 3/2013 | Riman | A61L 27/06 428/469 |
| 2014/0036464 A1 | 12/2014 | York et al. | |
| 2014/0364645 A1* | 12/2014 | York | B01J 35/002 560/211 |

FOREIGN PATENT DOCUMENTS

| | | | |
|---|---|---|---|
| JP | 7-196314 A | 8/1995 | |
| JP | 10-158255 A | 6/1998 | |
| JP | 10-259012 * | 9/1998 | ............ C01B 25/32 |
| JP | 10259012 A | 9/1998 | |
| JP | 200729464 A | 11/2007 | |
| WO | 2011031928 A1 | 3/2011 | |

OTHER PUBLICATIONS

Rosanna Gonzalez-McQuire, Jean-Yves Chane-Ching, E. Vignaud, A. Lebugle and Stephen Mann, "Synthesis and characterization of amino acid-functionalized hydroxyapatite nanorods", J. Mater Chem. 2004, 14, 2277-2281 (Abstract only, 1 page).

Sanosh Kunjalukkal Padmanabhan, Avinash Balakrishnan, Min-Cheol Chu, Yong Jin Lee, Taik Nam Kim, Seong-Jai Cho, "Sol-gel synthesis and characterization of hydroxyapatite nanorods", Particuology, vol. 7, p. 466-470, (2009) (5 pages).

Jingbing Liu, Kunwei Li, Hao Wang, Mankang Zhu Hui Yan, "Rapid formation of hydroxyapatite nanostructures by microwave irradiation", Chemical Physics Letters 2004, 396, 429 (Abstract only,1 page).

Jiing Di Chen, Ying Jun Wang, Kun Wei, Shu Hua Zhang, Xue Tao Shi, "Self-organization of hydroxyaptite nanorods through oriented attachment", Biomaterials 2007, 28, 2275 (Abstract only,1 page).

Takashi Tsuchida, Jun Kubo, Tetsuya Yoshioka, Shuji Sakuma, Tatsuya Takeguchi, Wataru Ueda, "Influence of Preparation Factors on Ca/P Ratio and Surface Basicity of Hydroxyapatite Catalyst", Journal of the Japan Petroleum Institute, vol. 52, No. 2, 51-59 (2009) (9 pages).

Jinhui Tao, Haihua Pan, Yaowu Zeng, Xurong Xu and Ruikang Tang, "Roles of Amorphous Calcium Phosphate and Biological Additives in the Assembly of Hydroxyapatite Nanoparticles", J Phys Chem. B, 2007 111 (47) pp. 13410-13418 (Abstract only,1 page).

Xing Zhang, Kenneth S. Vecchio, "Hydrothermal synthesis of hydroxyapatite rods" Journal of Crystal Growth, 2007 308, 133-140 (Abstract only,1 page).

Yingkai Liu, Dedong Hou, Guanghou Wang, "A Simple wet chemical synthesis and characterization of hydroxyapatite nanorods" Material Chemistry and Physics, 2004, 86, 69-73 (Abstract only, 1 page).

Kazuhiko Kandori, Kazuma Takeguchi, Masao Fukusumi, Yoshiaki Morisada, "Preparation and characterization of calcium hydroxyapatite and balloon-like calcium phosphate particles from forced hydrolysis of Ca(OH)2-triphosphate solution" Polyhedron 2009, 28, 3036 (Abstract only, 1 page).

International Search Report GB1019092.4 dated Sep. 1, 2011 (3 pages).

Russian Office Action fir RU2013126659 dated Aug. 20, 2013 (5 pages).

International Preliminary Report on Patentability from the International Bureau for International Application No. PCT/GB2011/052147 dated May 14, 2013 (8 pages).

European International Search Report for PCT/GB2011/052147 dated Feb. 7, 2012 (3 pages).

\* cited by examiner

Figure 2 TEM Image of Example 1 Crystals

Figure 3 TEM Image of Comparative Example 4

Figure 4 TEM image of example 3

Figure 5 TEM image of example 6 crystals

Figure 6 TEM image of example 8 crystals

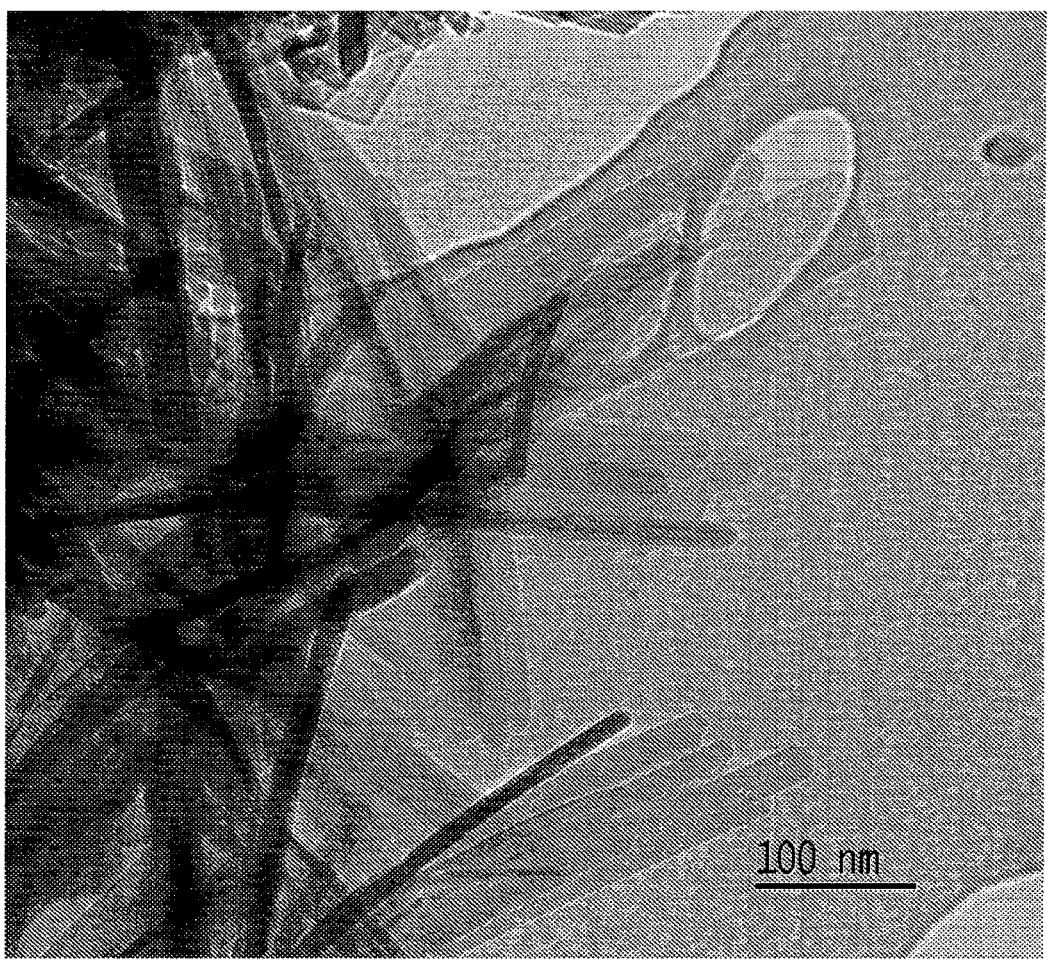
Figure 8 TEM Image of Example 11 at 100nm scale showing presence of nano-rods

PROCESS FOR THE PRODUCTION OF ETHYLENICALLY UNSATURATED CARBOXYLIC ACIDS OR ESTERS AND A CATALYST THEREFOR

TECHNICAL FIELD AND BACKGROUND OF THE INVENTION

The present invention relates to a process for the production of ethylenically unsaturated carboxylic acids or esters, particularly α, β unsaturated carboxylic acids or esters, more particularly acrylic acids or esters such as (alk)acrylic acids or alkyl (alk)acrylates particularly (meth)acrylic acid or alkyl (meth)acrylates by the condensation of carboxylic acid or esters with formaldehyde or a source thereof such as dimethoxymethane in the presence of catalysts, in particular, but not exclusively, a process for the production of (meth)acrylic acid or alkyl esters thereof, for example, methyl methacrylate, by the condensation of propionic acid or alkyl esters thereof with formaldehyde or a source thereof such as dimethoxymethane in the presence of such a catalyst system. The invention is particularly relevant to the production of methacrylic acid (MAA) and methyl methacrylate (MMA).

Such acids or esters may be made by reacting an alkanoic acid (or ester) of the formula $R^3$—$CH_2$—$COOR^4$, where $R^3$ and $R^4$ are each, independently, a suitable substituent known in the art of acrylic compounds such as hydrogen or an alkyl group, especially a lower alkyl group containing, for example, 1-4 carbon atoms, with a suitable methylene source such as formaldehyde. Thus, for instance, methacrylic acid or alkyl esters thereof, especially methyl methacrylate, may be made by the catalytic reaction of propionic acid, or the corresponding alkyl ester, e.g. methyl propionate, with formaldehyde as a methylene source in accordance with the reaction sequence 1.

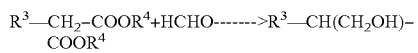

and

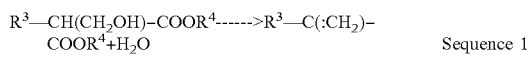  Sequence 1

An example of reaction sequence 1 is reaction sequence 2

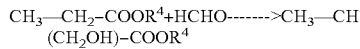

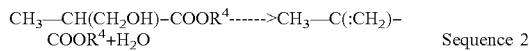  Sequence 2

A further reaction sequence is one which uses an acetal

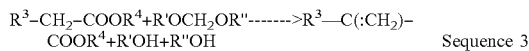  Sequence 3

A theoretical example of reaction sequence 3 is reaction sequence 4 which uses dimethoxymethane

  Sequence 4

The use of dimethoxymethane thus theoretically gives an anhydrous system which avoids the difficulty of subsequent water separation and/or subsequent product hydrolysis. In addition, the use of dimethoxymethane avoids the use of free formaldehyde but nevertheless acts in a general sense as a source of formaldehyde. The absence of water and free formaldehyde could greatly simplify the separation of MMA from the product stream.

However, in practice, Sequence 4 is problematic because methanol dehydrates to dimethyl ether and water. In addition, dimethoxymethane decomposes under catalytic conditions to dimethylether and formaldehyde. Any water formed in these reactions can hydrolyse the ester feedstock or product to its corresponding acid which may be undesirable.

U.S. Pat. No. 4,560,790 describes the production of α, β unsaturated carboxylic acids and esters by the condensation of methylal(dimethoxymethane) with a carboxylic acid or ester using a catalyst of general formula $M^1/M^2/P/O$ wherein $M^1$ is a group IIIb metal, preferably aluminium, and $M^2$ is a group IVb metal, preferably silicon.

As mentioned above, a known production method for MMA is the catalytic conversion of methyl propionate (MEP) to MMA using formaldehyde. A suitable catalyst for this is a caesium catalyst on a support, for instance, silica.

U.S. Pat. No. 4,118,588 discloses the production of methyl methacrylate and methacrylic acid by reacting propionic acid or methyl propionate with dimethoxymethane in the presence of catalysts based on the phosphates and/or silicates of magnesium, calcium, aluminium, zirconium, thorium and/or titanium and also in the presence of 0 to 0.5 moles of water per mole of the acetal. The preferred phosphates are aluminium, zirconium, thorium and titanium. The catalysts generally include an oxide modifier to improve the catalytic activity. Magnesium phosphate is not exemplified and calcium phosphate is not exemplified alone but one example with an oxide modifier is provided. The results are poor compared with the other phosphates, particularly aluminium.

Gupta et al in the Beilstein Journal of Organic Chemistry 2009, 5, No. 68 disclose the Knoevenagel condensation between aromatic aldehydes and malononitrile, ethyl cyanoacetate or malonic acid with hydroxyapatite supported caesium carbonate in water. However, the condensation with malonic acid resulted in decarboxylation.

Calcium hydroxyapatite exists in a number of crystalline forms. In addition, amorphous precursors of Hydroxyapatite, with calcium:phosphorus ratios which are similar to those for crystalline forms are disclosed. These can convert to crystalline Hydroxyapatite either by a physical or chemical treatment. The crystalline forms are generally divided into two types:—rods and plates but crystalline nanospheres are also known. These three crystal forms are well documented in the scientific literature. The typical natural rod-like and plate-like crystal forms of hydroxyapatite are disclosed in many documents for example in J Mater Chem 2004, 14, 2277, Rosanna Gonzalez-McQuire et al; Particuology 2009, 7, 466, Padmanabhan et al; Chemical Physics Letters 2004, 396, 429, Liu et al; Biomaterials 2007, 28, 2275, Chen et al; and Journal of the Japan Petroleum Institute 2009, 52, 51, Tsuchida et al.

Hydroxyapatite in the rod-like crystal form may develop structures such as bowknot-like or flower-like structures (Chemical Physics Letters 2004, 396, 429 by Liu).

The conditions for producing the various crystal forms of calcium hydroxyapatite are also well documented (J Mater Chem 2004, 14, 2277, Rosanna Gonzalez-McQuire et al; Particuology 2009, 7, 466, Padmanabhan et al; Chemical Physics Letters 2004, 396, 429, Liu et al; Biomaterials 2007, 28, 2275, Chen et al; Journal of the Japan Petroleum Institute 2009, 52, 51, Tsuchida et al; and J Phys Chem B 2007, 111, 13410, Tao et al). In addition, conversion of nano-spheres into rod-like and sheet-like structures has been disclosed by Tao et al (J Phys Chem B 2007, 111, 13410).

Specifically, methods for producing hydroxyapatite rods are well documented in the literature. Hydroxyapatite rods have been successfully synthesized using hydrothermal (Zhang et al., Journal of Crystal Growth, 2007, 308, 133-140), wet chemical (Materials Chemistry and Physics, 2004, 86, 69-73, Liu et al), ultrasonic spray pyrolysis (Materials Science and Engineering A, 2007, 449-451, 821-824, An et al) and sol-gel routes (Particuology 2009, 7, 466, Padmanabhan et al).

Most of the interest in the natural crystal forms of hydroxyapatite relates to its use or application in the study of biomedical applications due to its similarity to human bone. Few of the studies of morphological effects relate to industrial catalytic applications of hydroxyapatite.

Crystalline spheres or nano-spheres or amorphous calcium phosphates with calcium:phosphorus ratios similar to crystalline hydroxapatites in the form of spheres and nano-spheres are also well documented in the literature and are generally favoured by manufacturers (J Phys Chem B 2007, 111, 13410 Tao et al). Sometimes a crystalline core is encapsulated by an amorphous shell to create spheres. However, amorphous spheres can form initially followed by subsequent crystallisation as disclosed by Kandori et al (Polyhedron 2009, 28, 3036). Catalytic applications of hydroxyapatite are known but no mention of crystallinity or particular crystal forms is disclosed therein. Due to the wide availability of nano-spherical amorphous precursors or crystal forms of hydroxyapatite it can be assumed that the catalytic applications relate to this common amorphous or nano-spherical form unless otherwise mentioned.

Surprisingly, it has now been found that particular metal phosphates of a particular crystal form are remarkably selective catalysts for the production of a, ethylenically unsaturated carboxylic acid or esters by condensation of the corresponding acid or ester with a methylene source such as formaldehyde or dimethoxymethane providing high selectivity and low dimethylether (DME) production. In particular, the catalysts are particularly suited to the production of α, β ethylenically unsaturated carboxylic esters because they produce little water in such reactions.

BRIEF SUMMARY OF THE INVENTION

According to a first aspect of the present invention there is provided a method of producing an ethylenically unsaturated carboxylic acid or ester, preferably an α, β ethylenically unsaturated carboxylic acid or ester, comprising the steps of contacting formaldehyde or a suitable source thereof with a carboxylic acid or ester in the presence of a catalyst and optionally in the presence of an alcohol, wherein the catalyst comprises group II metal phosphate crystals having rod or needle like morphology or a suitable source thereof.

Suitable examples of phosphates in accordance with the present invention include hydroxyapatite, pyrophosphate, hydroxyphosphate, $PO_4^{2-}$ phosphate and mixtures thereof, more preferably, hydroxyapatite, pyrophosphate and mixtures thereof.

By the term "a suitable source thereof" in relation to the phosphate crystals is meant that the morphology may be formed in situ from the phosphate source under reaction conditions. Therefore, one phosphate may act as the source of another. For instance, the group II pyrophosphates may form the group II hydroxyapatites under reaction conditions and thus the pyrophosphate is a suitable source of the hydroxyapatite.

By the term "a suitable source thereof" in relation to formaldehyde is meant that the free formaldehyde may either form in situ from the source under reaction conditions or that the source may act as the equivalent of free formaldehyde under reaction conditions, for example it may form the same reactive intermediate as formaldehyde so that the equivalent reaction takes place.

The references to a rod like crystal morphology of metal phosphates is self explanatory to the skilled person but in case of doubt may be taken to indicate a crystal with preferential growth in one key dimension (the z axis) and a substantially lesser growth in the second and third dimension (the x and y axes). More specifically, a rod like crystal has a length, a width and a thickness. The z axis can be defined as the length. The x and y axes can be defined interchangeably as the width and thickness. The thickness to width ratio may be unequal. Alternatively the width:thickness ratio may be substantially equal, for example it may be between 1:2 and 2:1, more typically between 2:3 and 3:2 and most typically between 3:4 and 4:3. In any case, the thickness and width will be less than the length; wherein an aspect ratio of the length (z axis): thickness and/or width (x and y axes) is typically >2, more typically, >5, most typically, >10.

The rod like shape as defined in the present invention is intended to cover any crystal that has the above dimensions and therefore has the crystal habit or appearance, macroscopically or microscopically, of being in an elongated member form with likeness to a rod. Therefore, rod like shape covers any of the official crystal forms capable of a rod like crystal habit i.e. hexagonal, orthorhombic, tetragonal, monoclinic, triclinic or cubic. Preferably, the crystal form of the rod like crystals of the present invention is hexagonal.

Preferably, the group II metal of the phosphate of the invention may be a mixture of group II metals but is preferably selected from Ca, Sr or Ba or mixtures thereof, more preferably, Ca or Sr, especially, Ca. Particularly preferred catalysts are strontium pyrophosphate, strontium hydroxyapatite, barium hydroxyapatite and calcium hydroxyapatite which display rod like morphology in their crystal form, more preferred are strontium hydroxyapatite, barium hydroxyapatite and calcium hydroxyapatite, most preferred are strontium hydroxyapatite and calcium hydroxyapatite. The group II metal magnesium is more typically used as a doping metal with one or more of Ca, Sr or Ba in the phosphates of the present invention.

Preferably, the catalyst is at least 50% w/w metal phosphate, more preferably, at least 70% metal phosphate, most preferably, at least 80% metal phosphate. The metal phosphate has a significant crystalline metal phosphate fraction but may also include amorphous material. Known crystalline forms of the metal phosphates are rod/needle like, plate like or crystalline spheres. The inventors have surprisingly found that crystalline metal phosphates with at least some rod/needle like crystals have surprisingly high selectivity in the present invention.

The crystal morphology of the crystalline metal phosphate may be determined by techniques known to those skilled in the art, for example by transmission electron microscopy (TEM) or scanning electron microscopy (SEM), or from the relative intensities of XRD peaks by comparison with known morphological variants of the crystalline metal phosphates. Preferably, rod/needle like crystals are on average the dominant crystalline form numerically in the phosphate. Preferably, rod/needle like crystals are on average the dominant crystalline form by amount of average TEM image area covered in the phosphate. By dominant is meant that the crystalline form is the largest group of crystals. However, it is not necessary for the rod or needle like morphology to be the dominant crystalline form for the invention to be effective. Even a metal phosphate with a minority of the crystals in the rod or needle like form will be still effective as a catalyst. Accordingly, the group II metal phosphate crystals having the rod or needle like morphology or suitable source thereof need only be present or become present at a level that is effective to catalyse the reaction with sufficient selectivity such as those selectivities set out below.

Preferably, the selectivity of the reaction to ethylenically unsaturated carboxylic acid or ester, preferably α, β ethylenically unsaturated carboxylic acid or ester product, especially (alk)acrylic acid or alkyl (alk)acrylate product is at least 40 mole %, more preferably, at least 60 mole %, most preferably, at least 70 mole %, especially, at least 80 or 90 mole %. Typical selectivities as set out above are in the range 45-100 mole %, more preferably, 65-100 mole %, most preferably, 75-100 mole %, especially, 85 or 90-100 mole %. The mole % may be determined by gas chromatography. Selectivity is based on mole % of total product converted from the starting carboxylic acid or ester. For example, if 100 g methyl propionate reacts to produce 90 g of methyl propionate and 10 g of propionate derived product of which 9 g is methyl methacrylate then the reaction is 90% selective to methyl methacrylate by weight which may be converted to mole % selectivity using the relevant molecular weights to determine moles methyl propionate converted to product and moles of methyl methacrylate produced and calculating the mole % of methyl methacrylate therefrom. Similarly, the same analysis can be carried out for other components such as methacrylic acid. A suitable gas chromatography device is a Shimadzu GC GC2010, equipped with a RTX1701 column (supplied by Thames Restek UK Ltd) & a Flame Ionization Detector (FID).

Reactor feed compositions and samples of the condensed flow exiting the catalytic reactor may all be analysed by gas chromatography. A suitable device is the Shimadzu GC detailed above. For each analysis, the resultant chromatograph may be processed using Shimadzu's "GC Solutions" software to obtain peak areas for individual components. The FID response factors for the individual components obtained using standards are applied to convert peak areas, first into wt %, and then into mole %, of detectable material in the sample.

Water content in the product of the catalytic reaction may be measured by a Karl-Fischer titration (Mettler Toledo DL38, with a probe DM143-SC, Hydranal Working Medium K and Composite K).

Preferably, the rod like crystals are in a sufficiently open arrangement to provide access to their surfaces to effect sufficient catalysis. In a congealed mass of crystals the surface area of the rod like crystals available for catalysis may be reduced thus reducing although not removing catalytic effectiveness. Accordingly, the phosphate crystals of the invention are preferably, substantially non-agglomerated or non-congealed.

Preferably, at least 10% mol/mol of the total metal phosphate in the catalyst is in a crystalline form, more preferably, at least 30% mol/mol, most preferably, at least 50% mol/mol. Typically, amorphous material (or fraction of crystalline phase) can be estimated based on XRD results from the equation:

$$Xc = (1 - v112/300)/I300$$

where I300 is the intensity of the (3 0 0) diffraction peak and _v112/300 is the intensity of the hollow between the (1 1 2) and (3 0 0) diffraction peaks; Xc is the degree of crystallinity.

Generally, the crystal size of the metal phosphate crystals on the z axis is in the range $0.01\text{-}10^4$, more preferably, $0.1\text{-}10^4$ nm, most preferably, $0.1\text{-}10^3$ nm i.e. the crystals of the invention are typically nano-crystals. In particular, the rods are generally $0.001\text{-}10^3$ nm wide, more preferably, $0.01\text{-}10^3$ nm wide, most preferably, $0.1\text{-}10^2$ nm wide or thick and preferably have the aspect ratios defined herein. In preferred embodiments, the metal phosphate crystals on the z and x or y axis are in the respective ranges 1-5000 nm and 0.1 to 500 nm, more preferably, 5-1000 nm and 0.5 to 100 nm, most preferably, 10-500 nm and 1-50 nm. Accordingly, in this context, the morphology of the crystals of the invention may be termed nano-rods.

Advantageously, the use of metal phosphate catalyst in the process of the invention also results in surprisingly low levels of dimethyl ether in the product stream whether the formaldehydic component of the vaporised reactor feed composition is based on formaldehyde or dimethoxymethane.

It has also been found that the catalyst of the invention has increased effectiveness when the surface layer of the crystals is depleted below the optimum M:P ratio for hydroxyapatite i.e. below 1.67. Crystal surface M:P ratios of between 1.30 and 1.55 have been found to be particularly effective. By surface ratio herein we refer to the ratio as determined by X-ray photoelectron spectroscopy (XPS). However, it has also been found that the use of low M:P pre-cursor ratios can result in final crystals with increased surface M:P ratios above the bulk. Bulk crystal M:P ratios in the range 1-1.3 can result in increased surface M:P ratios correspondingly higher than those found in the bulk. Therefore, it may be that increased catalytic effectiveness is found as a result of a favoured metal phosphate surface arrangement. Typically, the M:P surface ratio, particularly that for Ca:P is in the range 1.30-1.55. This may be a metal hydroxyapatite structure depleted in metal.

It is possible that a particularly preferred metal hydroxyapatite formula of

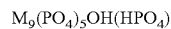

$$M_9(PO_4)_5OH(HPO_4)$$

is therefore highly catalytically active with a preferred ratio of M:P of 1.5, wherein the metal is a group II metal, more preferably, Ca, Sr or Ba, most preferably, Ca or Sr, especially, Ca or mixtures thereof.

The general formula of metal hydroxyapatite (HAP) in accordance with the invention may be given as formula I $$M_{10-x}(PO_4)_{6-x}(OH)_{2-x}(HPO_4)_x \qquad \text{I}$$

wherein M represents a group II metal, preferably, Ca, Sr or Ba or mixtures thereof, more preferably Ca or Sr or mixtures thereof, and wherein X is 0-1.

The general formula of metal pyrophosphate in accordance with the invention may be given as formula II $$M_2P_2O_7 \qquad \text{II}$$

wherein M represents a group II metal, preferably, Ca, Sr or Ba or mixtures thereof, more preferably, Ca or Sr or mixtures thereof.

As will be appreciated, the M:P mole ratio in a pure metal phosphate can be varied for example around the optimum ratio of 5:3 for metal hydroxyapatite and 1:1 for metal pyrophosphate. The metal hydroxyapatite is typically varied to be a metal deficient hydroxyapatite whereas the metal pyrophosphate may be varied to be metal rich. It is possible for the M:P mole ratio to vary between 0.8-1.8 but typical surface M:P ranges are 1.00-1.55, especially, 1.10-1.50, more especially, 1.20-1.50 as determined by XPS whereas bulk M:P mole ratios vary between 0.8-1.8, more typically, 1.00-1.70, as determined by X-Ray Fluorescence Spectrometry (XRF). A suitable instrument for determining surface M:P ratios by XPS is a Kratos "Axis Ultra" X-ray Photo-electron Spectrometer. A suitable instrument for determining bulk M:P ratios by XRF is an Oxford Instruments X-Supreme 8000 which is based on Energy Dispersive X Ray Fluorescence measurements (EDXRF).

Varying M:P ratios in the final crystals can be achieved by varying precursor M:P ratios and/or in the case of a wet production method, the solution pH and/or solution temperatures.

Generally, production of the rod or needle like morphology of the invention is achieved by appropriate methods known to the skilled person as already set out above.

A preferred production method for production of hydroxyapatite and pyrophosphate rod or needle like crystals according to the invention uses a simple wet method of combining the group II metal nitrate and diammonium hydrogenphosphate as metal and phosphorus precursors respectively in aqueous solution to form a precipitate. The combination of the nitrate and phosphate typically takes place between 20 and 115° C. The pH of the suspension during production is preferably kept between 4.5 and 13. Continuous stirring may maintain the product in suspension. After aging, the product is preferably dried and calcined at different temperatures ranging from 300 to 700° C. If more than one group II metal is present or if other metals are present the water-soluble metal salt (preferably nitrate) may be dissolved into the same solution as the first group II nitrate.

Other preferred methods include aqueous recrystallisation by forming the crystals on a substrate surface under the same temperature and pH conditions as the simple wet method above. Heating the catalyst precursors in steam (Steaming) at for example 120° C. with pH10 aqueous ammonia, or even under reaction conditions of 100-400° C. is also possible. Possible reagents for steaming with aqueous ammonia include a wide range of calcium phosphate compounds, preferably with Ca:P stoichiometry 1=<x=<1.5, such as dicalcium phosphate dihydrate (DCPD) or tricalcium phosphate (TCP).

Still further techniques include thermolysis, in a furnace at <700° C. For preparation by thermolysis, a physical mixture of thermally unstable calcium and phosphorus compounds (e.g. calcium nitrate, calcium hydroxide, diammonium hydrogen phosphate, phosphoric acid) is heated in a flow of air at temperatures up to 700° C.

The crystalline form of the HAP may be determined by TEM or XRD. Preferably, it is determined by TEM inspection and optionally confirmed by XRD. The absence or presence of crystallinity is preferably determined by XRD. A suitable instrument for XRD analysis is the Siemens Bruker D5000 Diffractometer D6. A suitable instrument for TEM analysis is a Philips CM12 Transmission Electron Microscope.

Crystalline HAP has characteristic XRD peaks at $2\theta°$ 25.9 (002), 31.9 (211), 32.3 (112) and 33.0 (300), all +/−0.2 $2\theta°$ According to a second aspect of the present invention there is provided a catalyst system comprising a crystalline metal phosphate catalyst and a catalyst support wherein the metal phosphate has rod/needle like morphology.

Advantageously, the rod/needle like morphology provides a surprisingly high selectivity for an ethylenically unsaturated acid or ester product in a catalysed reaction according to the first aspect of the present invention.

The rod/needle like crystal morphology of metal phosphates is self explanatory to the skilled person but in case of doubt may be taken to indicate a crystal with preferential growth along the z-axis. More specifically, a rod/needle like crystal has a length, a width and a thickness wherein the width and thickness ratio is between 1:2 and 2:1, more typically between 2:3 and 3:2 and most typically between 3:4 and 4:3. In any case, the thickness and width will always be far less than the length; wherein an aspect ratio of the length (z axis):thickness and/or width (x and y axes) is typically >2, more typically, >3, most typically, >5, especially >10.

Optionally, the catalytic performance and/or the level of rod/needle like morphology can be modified by changes applied to the catalyst synthesis conditions such as pH, temperature, pressure, M:P ratio and through doping with other elements, especially metals.

Typically, the catalyst synthesis pH may be from 4-13, more typically, from 4.5-12, most typically, from 5-11.5, especially, 6.5-11.5.

The wet synthesis solution temperature is not particularly critical and may be from 0-150° C., typically, from 10-130° C., more typically, from 20-125° C.

The pressure of reaction is also not critical and the catalyst can be prepared at reduced or high pressure. Typically, however, the catalyst is synthesised at or around atmospheric pressure.

Suitable doping elements may be present in the catalyst at a level up to 20 mol % of the metal M. Suitable doping metal cations are Cs, K, Rb, Na, Li, Zn, Ti, Si, Ln, Ce, Eu, Mg (if not used as a group II metal), Ba (if not used as a group II metal), Pb, Cd, Ag, Co, Cu, Ni and Zr. Preferred dopants are group I alkali metals and group II alkaline earth metals from the above list, more preferably, group I metals, especially Cs.

The doping cations may replace Ca, Sr and/or Ba in the above formulas.

Suitable doping anions may be present at a level of up to 20 mol % phosphate. Suitable doping anions are carbonate, chloride and fluoride. These may be assumed to partially replace the group II metal or phosphorus or hydroxide in the formulas herein as appropriate.

Preferably, the carboxylic acid or ester reactant of the present invention is of formula $R^3$—$CH_2$—$COOR^4$ wherein $R^4$ is either hydrogen or an alkyl group and $R^3$ is either hydrogen, an alkyl or aryl group.

Formaldehyde and Sources Thereof

A suitable source of formaldehyde may be a compound of formula I

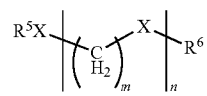

I wherein $R^5$ and $R^6$ are independently selected from $C_1$-$C_{12}$ hydrocarbons or H, X is O, n is an integer from 1 to 100, and m is 1.

Preferably, $R^5$ and $R^6$ are independently selected from $C_1$-$C_{12}$ alkyl, alkenyl or aryl as defined herein, or H, more preferably, $C_1$-$C_{10}$ alkyl, or H, most preferably, $C_1$-$C_6$ alkyl or H, especially, methyl or H. Preferably, n is an integer from 1 to 10, more preferably 1 to 5, especially, 1-3.

However, other sources of formaldehyde may be used including trioxane.

Therefore, a suitable source of formaldehyde includes any equilibrium composition which may provide a source of formaldehyde. Examples of such include but are not restricted to dimethoxymethane, trioxane, polyoxymethylenes $R^1$—O—$(CH_2$—O$)_i$—$R^2$ wherein $R^1$ and/or $R^2$ are alkyl groups or hydrogen, i=1 to 100, paraformaldehyde, formalin (formaldehyde, methanol, water) and other equilibrium compositions such as a mixture of formaldehyde, methanol and methyl propionate.

Typically, the polyoxymethylenes are higher formals or hemiformals of formaldehyde and methanol $CH_3$—O—$(CH_2$—O$)_i$—$CH_3$ ("formal-i") or $CH_3$—O—$(CH_2$—O$)_i$—H ("hemiformal-i"), wherein i=1 to 100, preferably, 1-5, especially 1-3, or other polyoxymethylenes with at least one non methyl terminal group. Therefore, the source of formaldehyde may also be a polyoxymethylene of formula $R^{31}$—O—$(CH2$-O—$)_i R^{32}$, where $R^{31}$ and $R^{32}$ may be the same or different groups and at least one is selected from a $C_1$-$C_{10}$ alkyl group, for instance $R^{31}$=isobutyl and $R^{32}$=methyl.

Preferably, the suitable source of formaldehyde is selected from dimethoxymethane, higher hemiformals of formaldehyde and methanol, $CH_3$—O—$(CH_2$—O$)_i$—H where i=2, formalin or a mixture comprising formaldehyde, methanol and methyl propionate.

It is particularly advantageous that dimethoxymethane can be used as a source of formaldehyde in the present invention. Advantageously, this provides the possibility of reacting dimethoxymethane with methyl propionate to form MMA and methanol without the production of water. This provides a potentially anhydrous system i.e. a system with reduced water side reactions and separation requirements than one using other sources of formaldehyde which contain or generate water. In addition, dimethoxymethane is stable, unlike other sources of formaldehyde which require water and methanol which then need to be taken into account in subsequent reaction and product separation. A further advantage of the present invention is the low level of decomposition in the present invention of dimethoxymethane to dimethylether and formaldehyde.

Preferably, by the term formalin is meant a mixture of formaldehyde:methanol:water in the ratio 25 to 65%:0.01 to 25%:25 to 70% by weight. More preferably, by the term formalin is meant a mixture of formaldehyde:methanol: water in the ratio 30 to 60%:0.03 to 20%:35 to 60% by weight. Most preferably, by the term formalin is meant a mixture of formaldehyde:methanol:water in the ratio 35 to 55%: 0.05 to 18%: 42 to 53% by weight.

Preferably, the mixture comprising formaldehyde, methanol and methyl propionate contains less than 5% water by weight. More preferably, the mixture comprising formaldehyde, methanol and methyl propionate contains less than 1% water by weight. Most preferably, the mixture comprising formaldehyde, methanol and methyl propionate contains 0.1 to 0.5% water by weight.

Preferably, the ethylenically unsaturated acid or ester produced by the process of the invention is selected from methacrylic acid, acrylic acid, methyl methacrylate, ethyl acrylate or butyl acrylate, more preferably, it is an ethylenically unsaturated ester, most preferably, methyl methacrylate.

The process of the invention is particularly suitable for the production of acrylic, alkacrylic, 2-butenoic, cyclohexenoic, maleic, itaconic and fumaric acids and their alkyl esters, and also methylene substituted lactones. Suitable, alkacrylic acids and their esters are ($C_{0-8}$alk)acrylic acid or alkyl ($C_{0-8}$alk)acrylates, typically from the reaction of the corresponding alkanoic acid or ester thereof with a methylene source such as formaldehyde in the presence of the catalyst, preferably the production of methacrylic acid or especially methyl methacrylate (MMA) from propanoic acid or methyl propionate respectively. Suitable methylene substituted lactones include 2-methylene valerolactone and 2-methylene butyrolactone from valerolactone and butyrolactone respectively.

The reaction of the present invention may be a batch or continuous reaction.

The term "alkyl" when used herein, means, unless otherwise specified, $C_1$ to $C_{12}$ alkyl and includes methyl, ethyl, ethenyl, propyl, propenyl butyl, butenyl, pentyl, pentenyl, hexyl, hexenyl and heptyl groups, preferably, the alkyl groups are selected from methyl, ethyl, propyl, butyl, pentyl and hexyl, more preferably, methyl. Unless otherwise specified, alkyl groups may, when there is a sufficient number of carbon atoms, be linear or branched, be cyclic, acyclic or part cyclic/acyclic, be unsubstituted, substituted or terminated by one or more substituents selected from halo, cyano, nitro, —$OR^{19}$, —$OC(O)R^{20}$, —$C(O)R^{21}$, —$C(O)OR^{22}$, —$NR^{23}R^{24}$, —$C(O)NR^{25}R^{26}$, —$SR^{29}$, —$C(O)SR^{30}$, —$C(S)NR^{27}R^{28}$, unsubstituted or substituted aryl, or unsubstituted or substituted Het, wherein $R^{19}$ to $R^{30}$ here and generally herein each independently represent hydrogen, halo, unsubstituted or substituted aryl or unsubstituted or substituted alkyl, or, in the case of $R^{21}$, halo, nitro, cyano and amino and/or be interrupted by one or more (preferably less than 4) oxygen, sulphur, silicon atoms, or by silano or dialkylsilcon groups, or mixtures thereof. Preferably, the alkyl groups are unsubstituted, preferably, linear and preferably, saturated.

The term "alkenyl" should be understood as "alkyl" above except at least one carbon carbon bond therein is unsaturated and accordingly the term relates to $C_2$ to $C_{12}$ alkenyl groups.

The term "alk" or the like should, in the absence of information to the contrary, be taken to be in accordance with the above definition of "alkyl" except "$C_0$ alk" means non-substituted with an alkyl.

The term "aryl" when used herein includes five-to-ten-membered, preferably five to eight membered, carbocyclic aromatic or pseudo aromatic groups, such as phenyl, cyclopentadienyl and indenyl anions and naphthyl, which groups may be unsubstituted or substituted with one or more substituents selected from unsubstituted or substituted aryl, alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$ or $C(S)NR^{27}R^{28}$ wherein $R^{19}$ to $R^{30}$ each independently represent hydrogen, unsubstituted or substituted aryl or alkyl (which alkyl group may itself be unsubstituted or substituted or terminated as defined herein), or, in the case of $R^{21}$, halo, nitro, cyano or amino.

The term "halo" when used herein means a chloro, bromo, iodo or fluoro group, preferably, chloro or fluoro.

The term "Het", when used herein, includes four- to twelve-membered, preferably four- to ten-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, alkyl (which alkyl group may itself be unsubstituted or substituted or terminated as defined herein) —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$ or —$C(S)N(R^{27})R^{28}$ wherein $R^{19}$ to $R^{30}$ each independently represent hydrogen, unsubstituted or substituted aryl or alkyl (which alkyl group itself may be unsubstituted or substituted or terminated as defined herein) or, in the case of $R^{21}$, halo, nitro, amino or cyano. The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

Suitable optional alcohols for use in the catalysed reaction of the present invention may be selected from a $C_1$-$C_{30}$ alkanol, including aryl alcohols, which may be optionally substituted with one or more substituents selected from alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)NR^{27}R^{28}$, $SR^{29}$ or $C(O)SR^{30}$ as defined herein. Highly preferred alkanols are $C_1$-$C_8$ alkanols such as methanol, ethanol, propanol, iso-propanol, iso-butanol, t-butyl alcohol, phenol, n-butanol and chlorocapryl alcohol, especially, methanol. Although the monoalkanols are most preferred, poly-alkanols, preferably, selected from di-octa ols such as diols, triols, tetra-ols and sugars may also be utilised. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl)ethane, nannose, sorbase, galactose and other sugars. Preferred sugars include sucrose, fructose and glucose. Especially preferred alkanols are methanol and ethanol. The most preferred alkanol is methanol. The amount of alcohol is not critical. Generally, amounts are used in excess of the amount of substrate to be esterified. Thus the alcohol may serve as the reaction solvent as well, although, if desired, separate or further solvents may also be used.

Typical conditions of temperature and pressure in the process of the first aspect of the invention are between 100° C. and 400° C., more preferably, 200° C. and 375° C., most preferably, 300° C. and 360° C.; between 0.001 MPa and 1 MPa, more preferably, 0.03 MPa and 0.5 MPa, most preferably, between 0.03 MPa and 0.3 MPa. Typical residence times for the reactants in the presence of the catalyst are between 0.1 and 300 secs, more preferably, 1-100 secs, most preferably, 2-30 secs, especially, 3-20 secs.

Advantageously, use of the catalyst of the present invention has been found to produce remarkably low levels of unwanted side products in the reaction of formaldehyde or a suitable source thereof with a carboxylic acid or ester to produce an ethylenically unsaturated carboxylic acid or ester. In particular, remarkably low levels of dimethyl ether (DME) are produced compared to conventional catalysts such as aluminium phosphate. In addition, the catalysts provide excellent selectivity and activity.

The amount of catalyst used in the process of the present invention is not necessarily critical and will be determined by the practicalities of the process in which it is employed. However, the amount of catalyst will generally be chosen to effect the optimum selectivity and yield. Nevertheless, the skilled person will appreciate that the minimum amount of catalyst should be sufficient to bring about effective catalyst surface contact of the reactants during the contact time. In addition, the skilled person would appreciate that there would not really be an upper limit to the amount of catalyst relative to the reactants but that in practice this may be governed again by the contact time required.

The relative amount of reagents in the process of the invention can vary within wide limits but generally the mole ratio of formaldehyde or suitable source thereof to the carboxylic acid or ester is within the range of 20:1 to 1:20, more preferably, 5:1 to 1:15, The most preferred ratio will depend on the form of the formaldehyde and the ability of the catalyst to liberate formaldehyde from the formaldehydic species. Thus highly reactive formaldehydic substances where one or both of $R^{31}$ and $R^{32}$ in $R^{31}O$—$(CH_2$—$O$—$)_iR^{32}$ is H require relatively low ratios, typically, in this case, the mole ratio of formaldehyde or suitable source thereof to the carboxylic acid or ester is within the range of 1:1 to 1:9. Where neither of $R^{31}$ and $R^{32}$ is H, as for instance in $CH_3O$—$CH_2$—$OCH_3$, or in trioxane higher ratios are most preferred, typically, 3:1 to 1:3.

As mentioned above, due to the source of formaldehyde, water may also be present in the reaction mixture. Depending on the source of formaldehyde, it may be necessary to remove some or all of the water therefrom prior to catalysis. Maintaining lower levels of water than that in the source of formaldehyde may be advantageous to the catalytic efficiency and/or subsequent purification of the products. Water at less than 10 mole % in the reactor is preferred, more preferably, less than 5 mole %, most preferably, less than 2 mole %.

The molar ratio of alcohol to the acid or ester is typically within the range 20:1 to 1:20, preferably 10:1 to 1:10, most preferably 5:1 to 1:5, for example 1:1. However the most preferred ratio will depend on the amount of water fed to the catalyst in the reactants plus the amount produced by the reaction, so that the preferred molar ratio of the alcohol to the total water in the reaction will be at least 1:1 and more preferably at least 3:1.

The reagents may be fed to the reactor independently or after prior mixing and the process of reaction may be continuous or batch. Preferably, however, a continuous process is used.

Typically, the reaction takes place in the gas phase. Accordingly, suitable condensing equipment is generally required to condense the product stream after reaction has taken place. Similarly, a vaporiser may be used to bring the reactants up to temperature prior to the catalyst bed. Preferably, the metal phosphate of the invention forms 50-100 wt % of the catalyst, more preferably, 55-100 wt %, most preferably, 60-100 wt %, especially, 70-100 wt %, more especially, 75-100 wt %, most especially, 80-100 wt % of the catalyst. The balance of the catalyst is made up of impurities, binders or inert materials. Generally, the metal phosphate forms about 80-90% of the catalyst. Included in the definition of metal phosphate is metal deficient phosphate having the M:P ratios defined herein.

When binder is used in the present invention it may form up to 50 wt % of the catalyst. Alternatively, the binder may be used in conjunction with a catalyst support to bind the catalyst to the support. In the latter case, the binder does not form part of the catalyst as such.

Suitable binders for the catalyst of the present invention will be known to those skilled in the art. Non-limiting examples of suitable binders include silica (including colloidal silica), silica-alumina, such as conventional silica-alumina, silica-coated alumina and alumina-coated silica, and alumina, such as (pseudo)boehmite, gibbsite, titania, titania-coated alumina, zirconia, cationic clays or anionic clays such as saponite, bentonite, kaolin, sepiolite or hydrotalcite or mixtures thereof. Preferred binders are silica, alumina and zirconia or mixtures thereof.

The metal phosphate particles can be embedded in the binder or vice versa. Generally, when used as part of the catalyst, the binder functions as an adhesive to hold the particles together. Preferably, the particles are homogeneously distributed within the binder or vice versa. The presence of the binder generally leads to an increase in mechanical strength of the final catalyst.

The typical average surface area of the metal phosphate catalyst is in the range 2-1000 $m^2\ g^{-1}$, more preferably, 5-400 $m^2\ g^{-1}$, most preferably, 10-300 $m^2\ g^{-1}$ as measured by the B.E.T. multipoint method using a Micromeritics TriStar 3000 Surface Area and porosity Analyser. The reference material used for checking the instrument performance is a carbon black powder supplied by Micromeritics with a surface area of 30.6 $m^2$/g (+/−0.75 $m^2$/g), part number 004-16833-00.

The typical average particle size of the catalyst particles is in the range 1 nm-10000 nm (10μ), more preferably, 5 nm-4000 nm (4μ), most preferably, 10 nm-3000 nm (3μ) as measured by a Malvern Zetasizer Nano S using dynamic light scattering and using NIST standards.

If the material is porous, it is preferably mesoporous with an average pore size of between 2 and 50 nm. Pore size can be determined by mercury intrusion porosimetry using NIST standards.

The average pore volume of the catalyst particles may be less than 0.01 $cm^3$/g but is generally in the range 0.01-5 $cm^3$/g as measured by nitrogen adsorption. However, microporous catalysts are not the most preferred because they may inhibit movement of reagents through the catalyst and a more preferred average pore volume is between 0.3-1.2 $cm^3$/g as measured by BET multipoint method using nitrogen adsorption according to ISO 15901-2:2006. The Micromeritics TriStar Surface Area and Porosity Analyser is used to determine pore volume as in the case of surface area measurements and the same standards are employed.

In the case of a non supported catalyst, the metal phosphate may be used directly in the form of a catalyst particles either free flowing or together with a suitable binder to create a solid of the desired shape and/or size. The particles may be of any suitable size and therefore also in the form of powder, granules or beads either with or without binder. Typically, the catalyst is used in the form of a fixed bed and for this purpose may be used alone or on a support and in the latter case may include a suitable catalytic binder to bind it to the support.

As mentioned above, the catalyst may be used on a support. In this case, the metal phosphate catalyst may form a suitable surface coating on a suitable support for a catalyst.

For the purposes of the present invention, the support does not form part of the catalyst.

The metal phosphates of the present invention are either unsupported or supported on a suitable support, for example, alumina, silica, silicon nitride, silicon carbide, colloidal silica, titania or aluminium phosphate.

It will be understood by the skilled person that a catalyst of the invention may be added to a support by any suitable means. The catalyst may be fixed, preferably by calcination, onto a suitable support after deposition of the compound onto the support using a suitable salt in a suitable solvent and subsequent drying of the surface coated support. Alternatively, the catalyst or suitable catalyst salt precursors may be co-precipitated with the support or suitable support precursors such as a silica sol from a suitable solvent. Preferably, an oxide support is used, more preferably, an oxide support as mentioned herein.

It is also possible to use the catalyst of the present invention in a mixture or admixture with another catalyst according to the present invention or otherwise with or without a suitable binder.

Generally, the metal phosphate of the present invention is a neutral molecule and therefore the negatively charged phosphate anions and optionally, hydroxide and any other non-metals balance the positively charged metals present.

The metal phosphate compound may be supported on a suitable support such as silica, silicon nitride, silicon carbide, colloidal silica, alumina, titania or aluminium phosphate. The support may or may not be an alkali metal doped support. If the support is alkali metal doped, the alkali metal doping agent may be selected from one or more of caesium, potassium, sodium, or lithium, preferably, caesium or potassium, more preferably, caesium. Alternatively, the metal phosphate may itself be doped with any one or more of the above mentioned doping metals.

Preferably, when a separate support for the catalyst of the first or second aspect is used, the weight ratio of catalyst: support is in the range 10:1 to 1:50, more preferably, 1:1 to 1:20, most preferably, 2:3 to 1:10. Advantageously, unsaturated ester selectivity is increased by doping cations having a low charge to radius ratio; thus caesium was found to be more selective than lithium. Preferably, therefore, if used, the doping metal cation is caesium, rubidium and/or potassium, more preferably, rubidium and/or caesium, most preferably caesium.

BRIEF DESCRIPTION OF THE DRAWINGS

Embodiments of the invention will now be described with reference to the following non-limiting examples and figures and by way of illustration only in which:—

FIG. 8 shows a TEM Image of Example 11 at 100 nm scale showing the presence of nano-rods.

DETAILED DESCRIPTION OF THE INVENTION

EXPERIMENTAL

Figure 1:
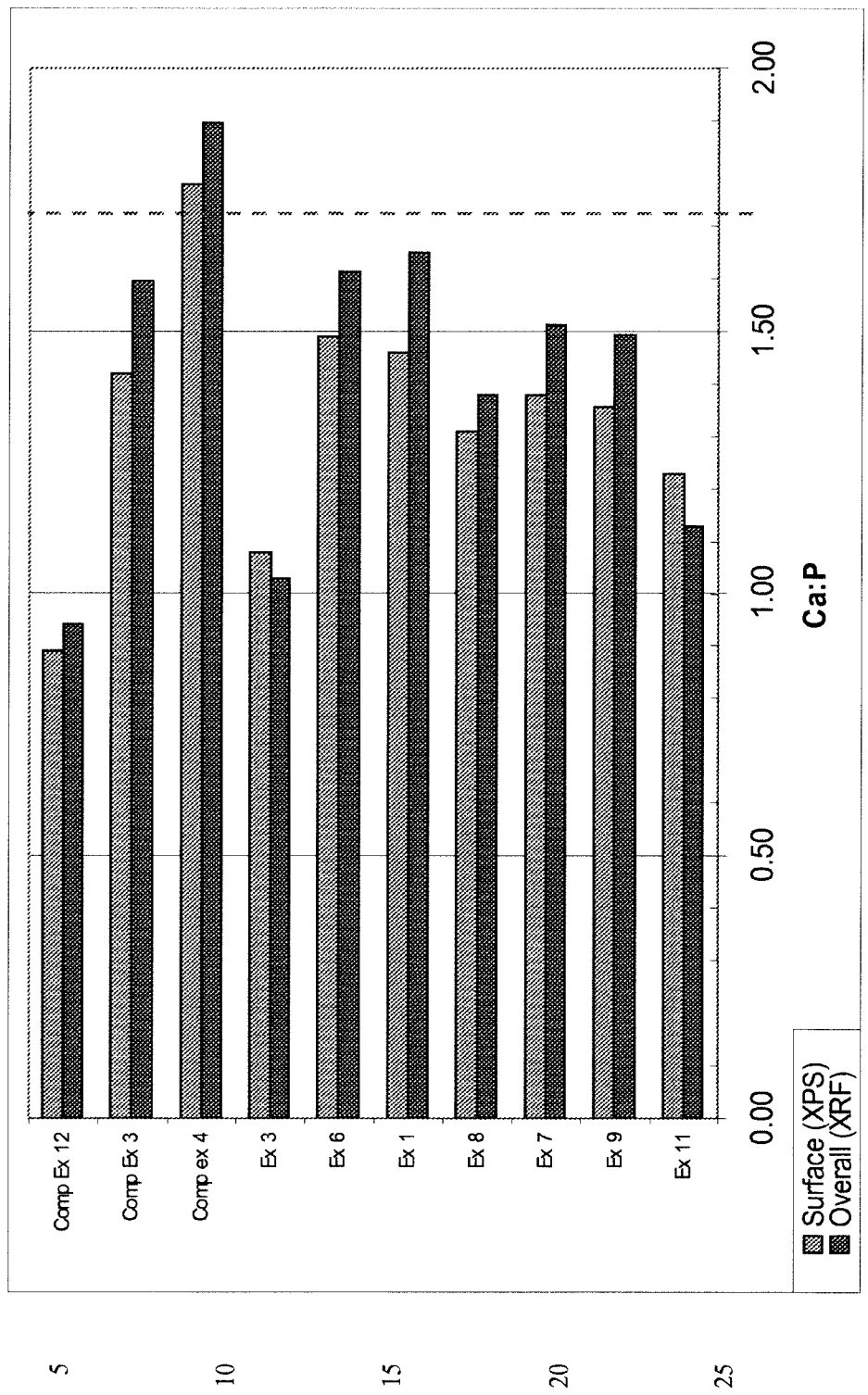
FIG. 1 shows the surface and bulk M:P ratios for a selection of samples.
Figure 2:
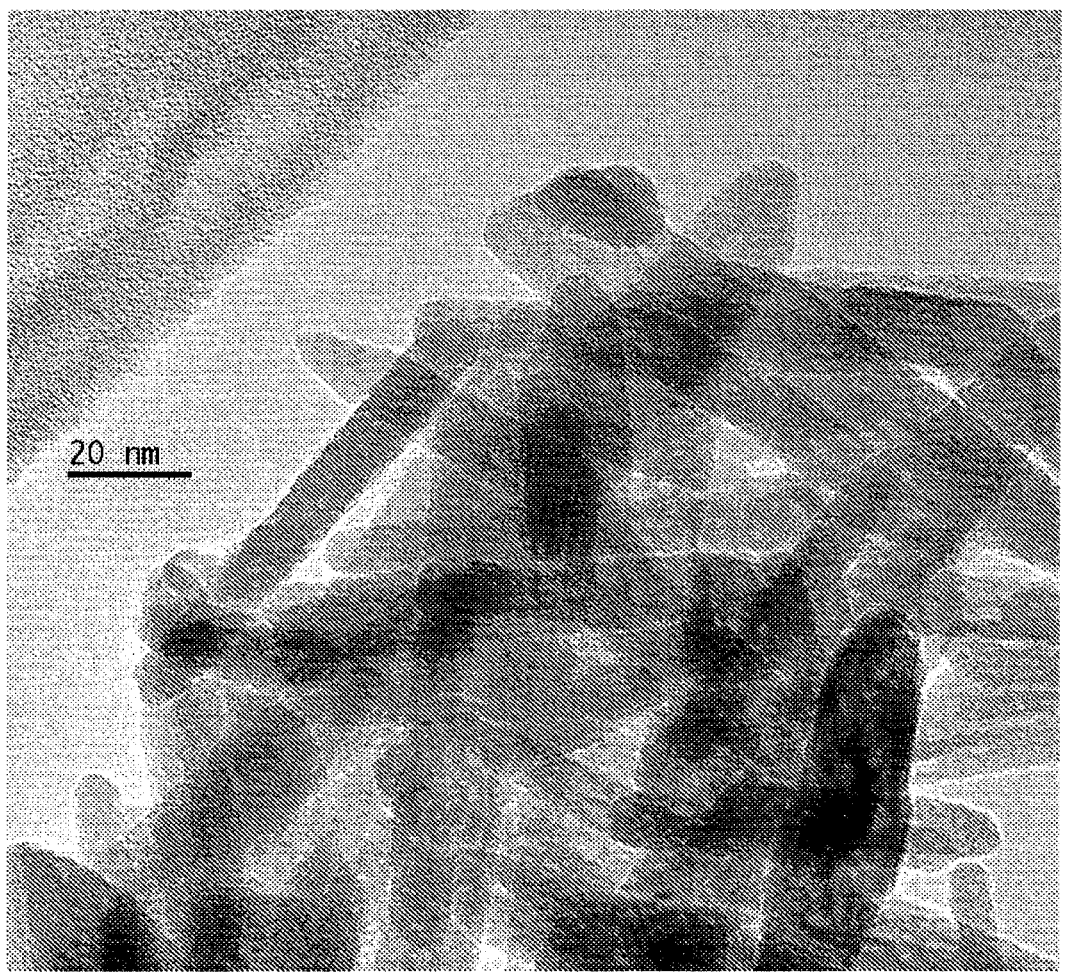
FIG. 2 shows the TEM Image of Example 1 crystals.
Figure 3:
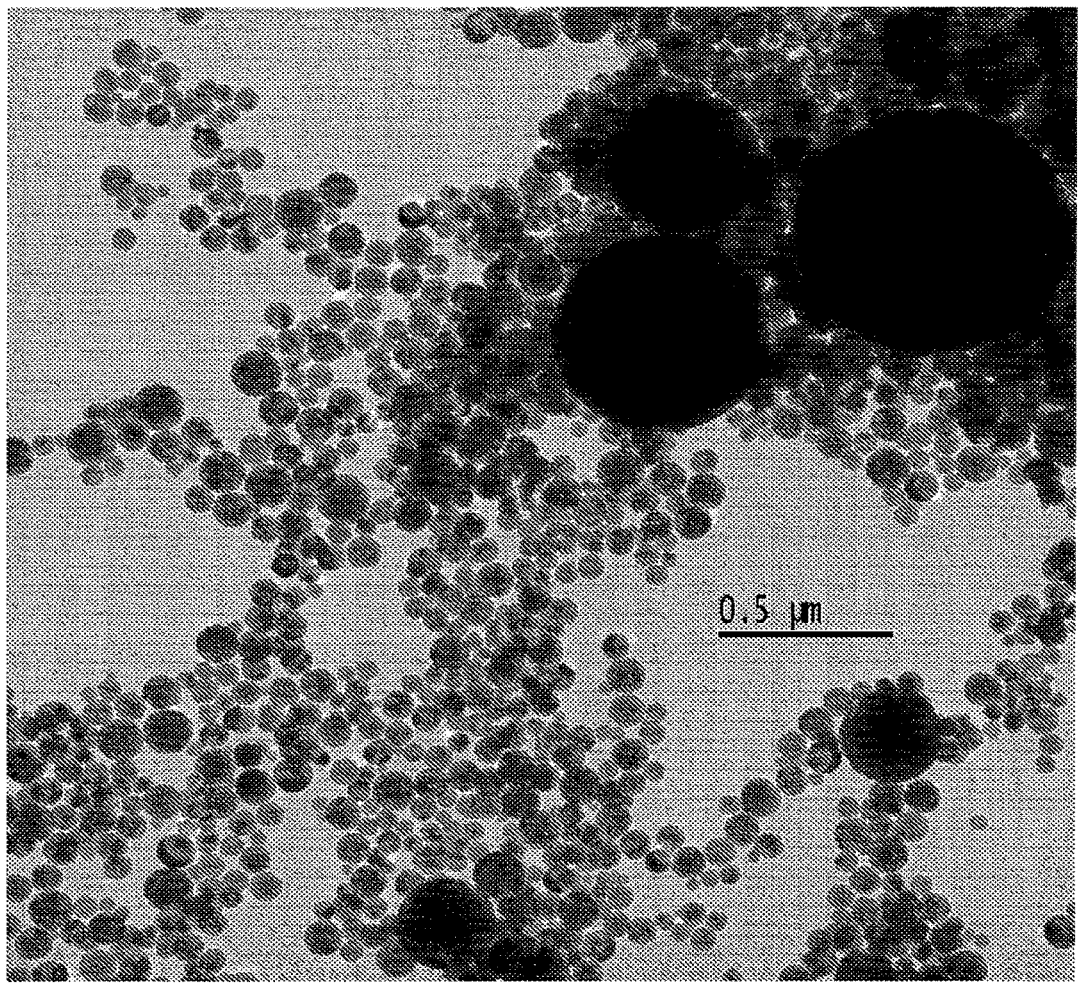
FIG. 3 shows the TEM Image of Comparative Example 4.
Figure 4:
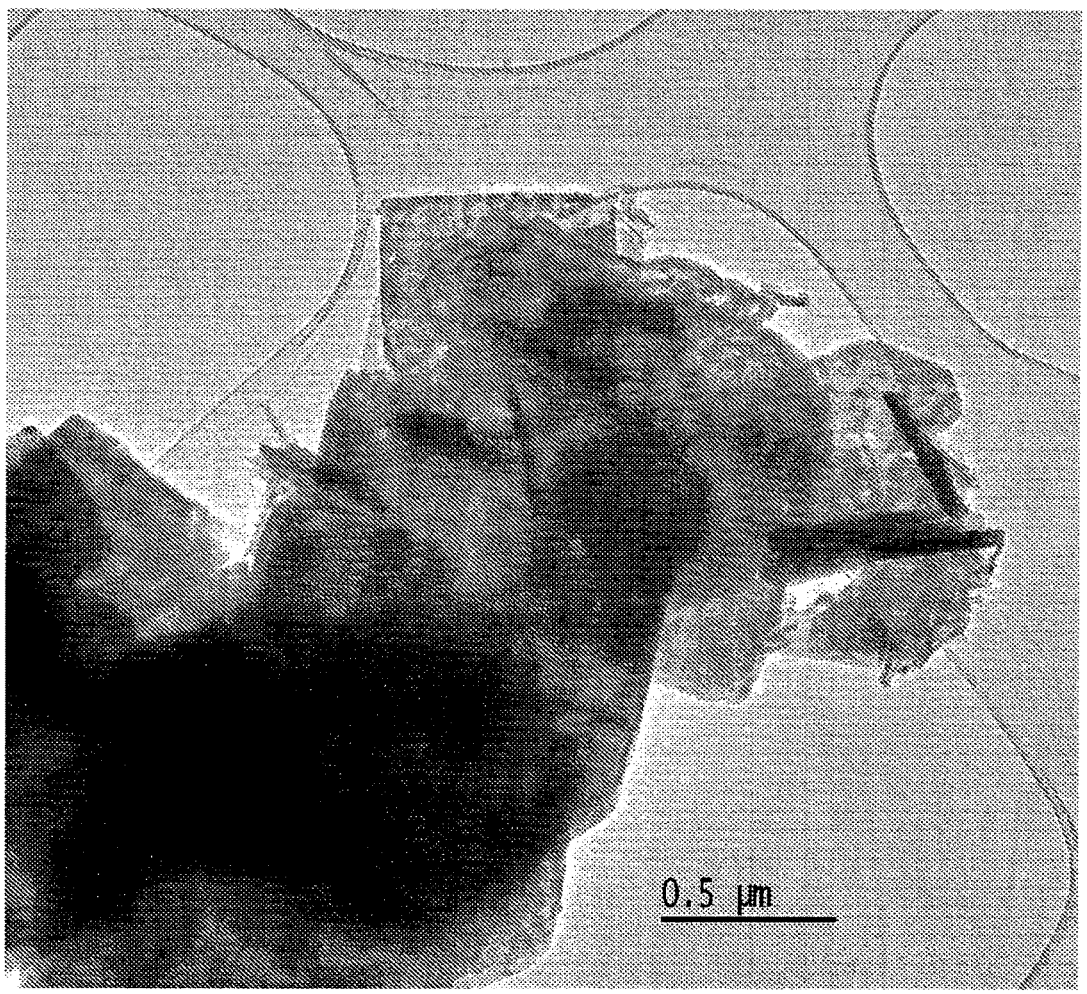
FIG. 4 shows the TEM image of example 3 crystals.
Figure 5:
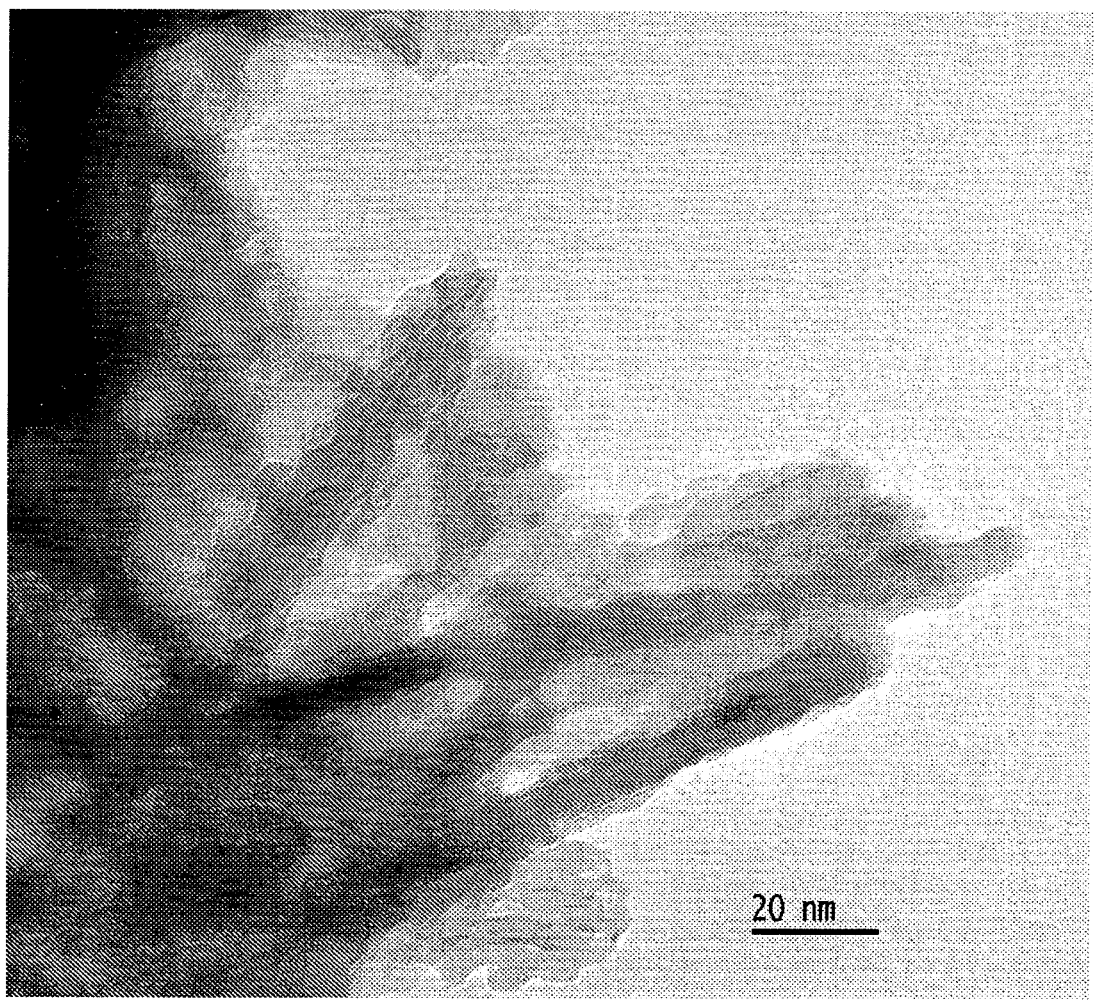
FIG. 5 shows the TEM image of example 6 crystals.
Figure 6:
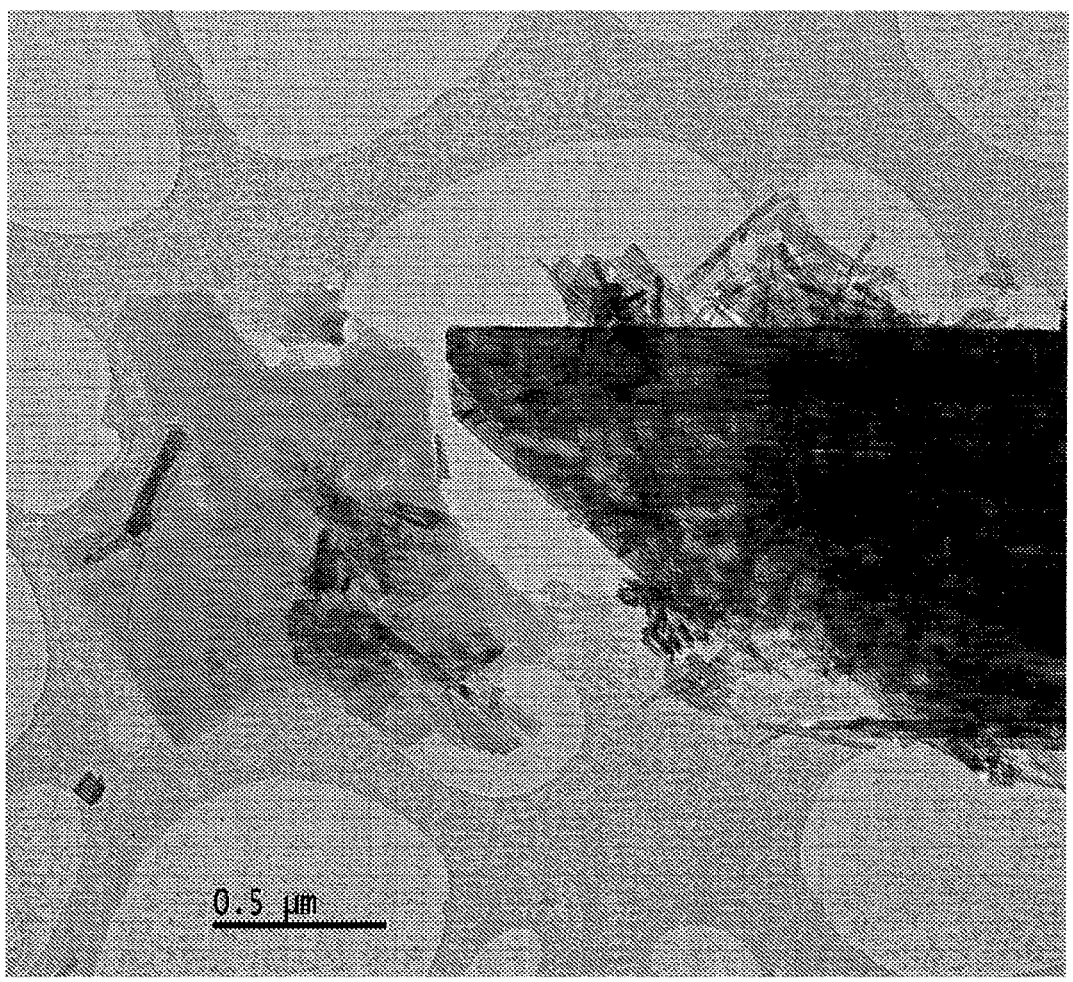
FIG. 6 shows the TEM image of example 8 crystals.

Analytical Methods
XRD Experimental
The samples were prepared as dry compressed powder thin layer specimens mounted on single silicon crystal discs. The following instrument and settings were used.

| | |
|---|---|
| Instrument | Siemens Bruker D5000 Diffractometer D6 |
| X-ray Tube | Cu LFF |
| Radiation | Ca Kα |
| Generator Voltage | 40 kV |
| Generator Current | 40 mA |
| Diffraction Geometry | Reflection Bragg Brentano |
| Variable Divergence Slit- | 12 mm irradiated length |
| Variable Antiscatter Slit- | 12 mm irradiated length |
| Receiving Slit | 0.2 mm |
| Primary soller slit | 2.3° |

-continued

| | |
|---|---|
| Detector Monochromator | Si/Li Energy dispersive (monochromating) Detector (Kα) |
| Step Size | 0.02° |
| Time per step | 3 seconds ("Sr$_2$P$_2$O$_7$ pH 7__1.67 " = 6 seconds) |
| Scan start angle | 1.5 |
| Scan finish angle | 90 |
| Specimen format | Bulk |
| Specimen loading | Compressed powder on silicon discs |
| Specimen spinning | Yes |
| Temperature | Ambient |

Data output is in the form of a diffractogram, showing reflection intensity (counts per second) vs. angle 2θ°. Crystalline phase identification is carried out by comparison to reference ICDD (formerly JCPDS) diffractograms. Peak intensity or peak broadening analysis is performed to quantify morphological parameters for a crystalline phase.

XRF Experimental

Powder samples were ground and sieved to achieve particle size <100 μm (mesh). Approximately 1 gram of powder was lightly compacted into a primary sample cup with a thin film transmission base. The primary cup was held within the instrument by a secondary safety cup also with a thin film transmission base. The following instrument and conditions were used.

| | |
|---|---|
| Instrument (EDXRF) | Oxford Instruments X-Supreme 8000 |
| X-ray source | Tungsten |
| Source Energy | 6 keV |
| Tube Current | 10 μA |
| Chamber purge gas | Helium |
| Detector (SDD) | Silicon Drift proportional detector |
| Primary cup base | Poly4 film (4 μm thick) |
| Secondary cup base | Poly4 film (4 μm thick) |
| Specimen spinning | Yes |
| Temperature | Ambient |
| Repeat scans | 3 |

Ca Kα and P Kα fluorescence intensities (counts per second) were recorded. The ratio of peak intensities was converted to give a Ca:P ratio for the material, using a calibration scale obtained from the Ca Kα and P Kα signals for stoichiometric reference materials.

XPS Experimental

A microspatula of the powder sample was placed onto a piece of silicone-free tape attached to the instrument sample holder, and the loose powder gently flattened with the microspatula tip. The following instrument and settings were used.

| | |
|---|---|
| Instrument | Kratos "Axis Ultra" X-ray Photoelectron Spectrometer |
| X-ray source | Al Kα |
| Monochromator | Yes |
| Pass Energy- | 160 eV (survey scan), 40 eV&10 eV(high-res scan) |
| Spot size | Ellipitic area, ~300 μm × ~700 μm. |
| Repeat scans | 2 |

Established Electron Spectroscopy for Chemical Analysis (ESCA) methods were utilised for qualification of the surface composition by elemental atomic percentage. Signal depth for oxide materials was ca. 3-5 nm, and the detection limit was about 1 atom in 1000 (i.e. 0.1 atom %, or 1000 ppm). Ca:P ratios were initially calculated from the experimental atomic percentages, and subsequently corrected for the presence of surface carbonaceous species.

TEM Experimental

Powder samples of the materials were suspended in water and drops were applied to copper grids bearing Lacey carbon support films. After drying, these were examined in a Philips CM12 TEM at an accelerating voltage of 120 kV.

Micrographs and electron diffraction patterns were collected at matching magnifications/tube-lengths. Selected regions were analysed using the associated NORAN Vantage EDX system. The variety of morphologies, compositions and crystalline species observed were recorded as images. The following instrument and settings were used.

Instrument-Philips CM12 Transmission Electron Microscope Accelerating Voltage 120 kV Two sets of experiments were run against various prepared examples of the invention and comparative examples. The first series of experiments were run using formaldehyde as a feed stream and the second series were run using dimethoxymethane as a feed stream. Analysis was carried out by gas chromatography, formaldehyde titration and with Karl Fischer apparatus. The analytical data were used to calculate the yield and selectivity of MMA+MAA. The selectivities in mole % relative to mole % MMA+MAA of diethylketone (DEK), dimethyl ether (DME) and toluene by-products are also tabulated in the catalyst test results below.

A Formaldehyde Feed

TABLE 1

| | Catalyst composition | Contact time [s] | MMA + MAA yield [%] | MAA selectivity [mole %] | MMA + MAA selectivity [mole %] | DME [mole %] | DEK [mole %] | Toluene [mole %] |
|---|---|---|---|---|---|---|---|---|
| Ex 1 | Ca-HAp pH7__1.67 | 10.3 | 4.1 | 1.3 | 93.5 | 0.5 | 0.0036 | 0.00014 |
| Ex 2 | Ca-HAp pH9-10__1.67 | 5.0 | 4.3 | 0.6 | 84.6 | 0.6 | 0.0040 | 0.00009 |
| Ex 3 | Ca-PO pH9-10__1.67__120 | 11.4 | 3.3 | 0.8 | 92.1 | 0.6 | 0.0026 | 0.00009 |
| Ex 4 | Ca-HAp pH7__1.67__EtOH | 7.1 | 2.8 | 3.7 | 93.7 | 3.1 | 0.0014 | 0.00018 |
| Ex 5 | Ca-HAp pH7__1.67__1% Cs | 6.9 | 4.1 | 0.3 | 93.6 | 0.2 | 0.0014 | 0.00007 |
| Comp Ex 1 | AlPO__TiO$_2$__B__urea | 3.1 | 4.7 | 12.6 | 69.2 | 14.4 | 0.0609 | 0.00528 |
| Comp Ex 2 | AlPO | 1.5 | 4.8 | 12.9 | 78.0 | 10.6 | 0.0457 | 0.00446 |

TABLE 1-continued

| | Catalyst composition | Contact time [s] | MMA + MAA yield [%] | MAA selectivity [mole %] | MMA + MAA selectivity [mole %] | DME [mole %] | DEK [mole %] | Toluene [mole %] |
|---|---|---|---|---|---|---|---|---|
| Comp Ex 3 | Comm Ca-HAp 289396 | 7.0 | 0.2 | 0.1 | 72.3 | 0.2 | 0.0004 | 0.00005 |
| Comp ex 4 | Comm Ca-HAp 677418 | 10.1 | 0.1 | 1.4 | 11.4 | 0.0021 | 0.0025 | 0.00000 |

Example 1

Preparative Example 1

23.6 g of calcium nitrate tetrahydrate $Ca(NO_3)_2 \cdot 4H_2O$ was dissolved in 100 ml of demineralised water and pH was adjusted to 7 with ammonium hydroxide. 7.9 g of diammonium hydrogen phosphate $(NH_4)_2HPO_4$ dissolved in 50 ml of demineralised water at pH 7 was added dropwise to the solution of calcium nitrate at the temperature of 80° C. while stirring. A suspension forms on addition of the phosphate to the nitrate solution. This mother suspension was continuously stirred for 3 hrs after the dropwise addition was complete and pH was maintained at 7 with ammonium hydroxide throughout. After that the suspension was filtered and washed with demineralised water. Then it was dried at 110° C. overnight and calcined in air at 400° C. for 1 hr. BET surface area of the material was 44 m²/g. The sample was identified as a crystalline hydroxyapatite type by XRD analysis. Some amorphous material was found. TEM confirmed the presence of rod like crystal form.

Catalyst testing: 3 g of catalyst as prepared in preparative example 1 was placed in a stainless steel tubular reactor connected to a vaporiser. The reactor was heated to 350° C. and vaporiser to 300° C. The mixture of 56.2 mole % of methyl propionate, 33.7 mole % of methanol, 9.6 mole % of formaldehyde and 0.5 mole % of water was passed through with the contact time indicated. The condensed reaction mixture was analysed by gas chromatography using a Shimadzu GC, equipped with a DB1701 column & a Flame Ionization Detector. For each analysis, the resultant chromatograph is processed using Shimadzu's GCsolution software to obtain peak areas for individual components. FID response factors for the individual components are applied to convert peak areas, first into wt %, and then into mol %, of detectable material in the sample.

Selectivity with respect to MAA or MAA+MMA is calculated from the molar amount of the component produced (exit molar content, less feed molar content), as percentage of the molar amount of propionate converted to products.

Example 2

Preparative Example 2

23.6 g of calcium nitrate tetrahydrate $Ca(NO_3)_2 \cdot 4H_2O$ was dissolved in 100 ml of demineralised water and pH was adjusted to 9-10 with ammonium hydroxide. 7.9 g of diammonium hydrogen phosphate $(NH_4)_2HPO_4$ in 50 ml of demineralised water at pH 9-10 was added dropwise to the solution of calcium nitrate at the temperature of 80° C. while stirring. A suspension forms on addition of the phosphate to the nitrate solution. This mother suspension was continuously stirred for 3 hrs after the dropwise addition was complete and pH was maintained at 9-10 with ammonium hydroxide throughout. After that the suspension was filtered and washed with demineralised water. Then it was dried at 110° C. overnight and calcined in air at 400° C. for 1 hr.

The preparative example 2 catalyst was tested as described in example 1.

Example 3

Preparative Example 3

23.6 g of calcium nitrate tetrahydrate $Ca(NO_3)_2 \cdot 4H_2O$ was dissolved in 100 ml of demineralised water and pH was adjusted to 9-10 with ammonium hydroxide. 7.9 g of diammonium hydrogen phosphate $(NH_4)_2HPO_4$ in 50 ml of demineralised water at pH 9-10 was added dropwise to a boiling solution of the calcium nitrate while stirring. A suspension forms on addition of the phosphate to the nitrate solution. This mother suspension was continuously stirred for 3 hrs after the dropwise addition was complete, then filtered and washed with demineralised water. After that it was dried at 110° C. overnight and then calcined in air at 400° C. for 1 hr. BET surface area of the material was 9 m²/g. The sample was identified as monetite and pyrophosphate by XRD analysis. TEM confirmed the presence of plate, rod, leaf and sphere like crystal forms.

The catalyst was tested as described in example 1.

Example 4

Preparative Example 4

23.6 g of calcium nitrate tetrahydrate $Ca(NO_3)_2 \cdot 4H_2O$ was dissolved in 100 ml of demineralised water and 100 ml of ethanol mixture. 7.9 g of diammonium hydrogen phosphate $(NH_4)_2HPO_4$ in 100 ml of demineralised water was added dropwise to the solution of calcium nitrate at the temperature of 25° C. while stirring. A suspension forms on addition of the phosphate to the nitrate solution. This mother suspension was continuously stirred overnight after the dropwise addition and pH was maintained at 7 with ammonium hydroxide throughout. After that the suspension was filtered and washed with demineralised water. Then it was dried at 110° C. overnight and calcined in air at 400° C. for 1 hr. BET surface area of the material was 73 m²/g. The sample was identified as a crystalline hydroxyapatite type by XRD analysis. Some amorphous material was found. TEM confirmed the presence of rod like crystal form. The catalyst was tested as described in example 1.

Example 5

Preparative Example 5

3 g of the catalyst prepared as in preparative example 1 was impregnated with 1 wt % of caesium using caesium acetate in methanol and tested as described in example 1.

Comparative Example 1

Preparative Comparative Example 1

The catalyst was synthesised following the preparation method disclosed in U.S. Pat. No. 4,118,588 patent in Example 4.

3 g of titanium dioxide $TiO_2$ (Aldrich catalogue number 634662), 2.3 g of aluminium phosphate (prepared as in comparative example 2) and 0.75 g of boric acid $H_3BO_3$ were mixed together. A paste was produced by addition of 0.25 g of urea in 5 ml of demineralised water. The paste was dried for 2 hrs at 120° C. and then heated for 4 hrs at 600° C.

The catalyst was tested as described in example 1. Modest selectivity was observed but a high level of DME was found.

Comparative Example 2

Preparative Comparative Example 2

37.5 g of aluminium nitrate nonahydrate $Al(NO_3)_3.9H_2O$ and 13.2 g of diammonium hydrogen phosphate $(NH_4)_2HPO_4$ were dissolved together in 160 ml of demineralised water acidified with nitric acid $HNO_3$. Solution of ammonium hydroxide was added until pH 7 was reached. Formed hydrogel was mixed for further 1 hr, after that it was filtered and washed with water. It was dried at 80° C. overnight and then calcined in air at 600° C. for 1 hr. BET surface area of the material was 181 m²/g.

The catalyst was tested as described in example 1. Modest selectivity was observed but a high level of DME was found.

Comparative Example 3

Commercial Ca-hydroxyapatite was used from Aldrich with catalogue number of 289396. The sample was confirmed as a crystalline hydroxyapatite type by XRD analysis. Some amorphous material was found. TEM showed the presence of agglomerated irregular sphere like particles.

The catalyst was tested as described in example 1. The results are shown in table 1. Although selectivity was modest and DME was low the yield was very low indicating a high level of inactivity.

Comparative Example 4

Commercial Ca-hydroxyapatite was used from Aldrich with catalogue number of 677418.

The samples were confirmed as crystalline hydroxyapatite type by XRD analysis. TEM showed evenly-shaped nano-spheres, typically 50-100 nm diameter (although with some individual spheres of 300-800 nm diameter), with no evidence of any non-spherical morphology.

The catalyst was tested as described in example 1. The results are shown in table 1. The yield and selectivity were both very low.

TABLE 2

| Ex. | Catalyst composition | Contact time [s] | MMA + MAA yield [%] | MAA selectivity [%] | MMA + MAA selectivity [%] | DME [mole %] | DEK [mole %] | Toluene [mole %] |
|---|---|---|---|---|---|---|---|---|
| Ex 6 | Ca-HAp pH11_1.67 | 1.2 | 1.6 | 0.2 | 80.0 | 0.1 | 0.0020 | 0.00015 |

Example 6

Preparative Example 6

23.6 g of calcium nitrate tetrahydrate $Ca(NO_3)_2.4H_2O$ was dissolved in 100 ml of demineralised water and pH was adjusted to 11 with ammonium hydroxide. 7.9 g of diammonium hydrogen phosphate $(NH_4)_2HPO_4$ in 50 ml of demineralised water at pH 11 was added dropwise to the solution of calcium nitrate at the temperature of 80° C. while stirring. A suspension forms on addition of the phosphate to the nitrate solution. This mother suspension was continuously stirred for 3 hrs after the dropwise addition was complete and pH was maintained at 11 with ammonium hydroxide throughout. After that the suspension was filtered and washed with demineralised water. Then it was dried at 110° C. overnight and calcined in air at 400° C for 1 hr. BET surface area of the material was 96 m²/g.

The sample was identified as a crystalline hydroxyapatite type by XRD analysis, although the presence of some amorphous material was indicated. TEM showed highly crystalline nano-rod structures grouped in bundles of similar orientation.

The catalyst was tested as described in example 1. The results are shown in table 2.

TABLE 3

| Ex. | Catalyst composition | Contact time [s] | MMA + MAA yield [%] | MAA selectivity [%] | MMA + MAA selectivity [%] | DME [mole %] | DEK [mole %] | Toluene [mole %] |
|---|---|---|---|---|---|---|---|---|
| Ex 7 | Ca-HAp pH7_1.5 | 10.27 | 4.4 | 1.7 | 92.0 | 2.6 | 0.0020 | 0.00014 |

TABLE 3-continued

| Ex. | Catalyst composition | Contact time [s] | MMA + MAA yield [%] | MAA selectivity [%] | MMA + MAA selectivity [%] | DME [mole %] | DEK [mole %] | Toluene [mole %] |
|---|---|---|---|---|---|---|---|---|
| Ex 8 | Ca-HAp pH7_1 | 3.0 | 1.6 | 1.6 | 92.3 | 1.2 | 0.0007 | 0.00015 |

Example 7

Preparative Example 7

14.2 g of calcium nitrate tetrahydrate $Ca(NO_3)_2 \cdot 4H_2O$ was dissolved in 100 ml of demineralised water and pH was adjusted to 7 with ammonium hydroxide. 5.3 g of diammonium hydrogen phosphate $(NH_4)_2HPO_4$ in 100 ml of demineralised water at pH 7 was added dropwise to the solution of calcium nitrate at the temperature of 80° C. while stirring. A suspension forms on addition of the phosphate to the nitrate solution. This mother suspension was continuously stirred for 3 hrs after the dropwise addition was complete and pH was maintained at 7 with ammonium hydroxide throughout. After that the suspension was filtered and washed with demineralised water. Then it was dried at 110° C. overnight followed by calcination in air at 400° C. for 1 hr. BET surface area of the material was 64 m²/g. The sample was identified as a crystalline hydroxyapatite type by XRD analysis. Some amorphous material was found.

The catalyst was tested as described in example 1.

Example 8

Preparative Example 8

14.2 g of calcium nitrate tetrahydrate $Ca(NO_3)_2 \cdot 4H_2O$ was dissolved in 100 ml of demineralised water and pH was adjusted to 7 with ammonium hydroxide. 7.9 g of diammonium hydrogen phosphate $(NH_4)_2HPO_4$ in 100 ml of demineralised water at pH 7 was added dropwise to the solution of calcium nitrate at the temperature of 80° C. while stirring. A suspension forms on addition of the phosphate to the nitrate solution. This mother suspension was continuously stirred for 3 hrs after the dropwise addition was complete and pH was maintained at 7 with ammonium hydroxide throughout. After that the suspension was filtered and washed with demineralised water. Then it was dried at 110° C. overnight followed by calcination in air at 400° C. for 1 hr. BET surface area of the material was 58 m²/g. The major phase was identified as a crystalline hydroxyapatite type by XRD analysis. A trace phase similar to calcium hydrogen phosphate $CaHPO_4$ was present. Some amorphous material was found. TEM showed the presence of rod and sheet like crystal forms.

The catalyst was tested as described in example 1. The results are shown in table 3.

TABLE 4

| Ex. | Catalyst composition | Contact time [s] | MMA + MAA yield [%] | MAA selectivity [%] | MMA + MAA selectivity [%] | DME [mole %] | DEK [mole %] | Toluene [mole %] |
|---|---|---|---|---|---|---|---|---|
| Ex 9 | Ca-HAp pH7_1.67_25 | 10.4 | 4.1 | 2.8 | 89.8 | 3.1 | 0.0017 | 0.00008 |
| Ex 10 | Ca-HAp pH11_1.00 | 9.8 | 4.8 | 4.0 | 91.4 | 4.7 | 0.0033 | 0.00011 |
| Ex 11 | Ca-PO pH5_1.67 | 15.6 | 4.4 | 1.4 | 94.6 | 0.42 | 0.002 | 0.00024 |
| ex 12 | Ca-PO pH5_1.00 | 6.9 | 3.1 | 1.4 | 90.1 | 1.8 | 0.0023 | 0.00008 |

Example 9

Preparative Example 9

23.6 g of calcium nitrate tetrahydrate $Ca(NO_3)_2 \cdot 4H_2O$ was dissolved in 100 ml of demineralised water and pH was adjusted to 7 with ammonium hydroxide. 7.9 g of diammonium hydrogen phosphate $(NH_4)_2HPO_4$ in 50 ml of demineralised water at pH 7 was added dropwise to the solution of calcium nitrate at the temperature of 25° C. while stirring. A suspension forms on addition of the phosphate to the nitrate solution. This mother suspension was continuously stirred for 3 hrs after the dropwise addition was complete and pH was maintained at 7 with ammonium hydroxide throughout. After that the suspension was filtered and washed with demineralised water. Then it was dried at 110° C. overnight and calcined in air at 400° C. for 1 hr. TEM showed short crystalline nano-rods <100 nm in length, and some amorphous material. The catalyst was tested as described in Example 1. The results are shown in Table 4.

Example 10

Preparative Example 10

14.2 g of calcium nitrate tetrahydrate $Ca(NO_3)_2 \cdot 4H_2O$ was dissolved in 100 ml of demineralised water and pH was adjusted to 11 with ammonium hydroxide. 7.9 g of diammonium hydrogen phosphate $(NH_4)_2HPO_4$ in 50 ml of demineralised water at pH 11 was added dropwise to the solution of calcium nitrate at the temperature of 80° C. while stirring. A suspension forms on addition of the phosphate to the nitrate solution. This mother suspension was continuously stirred for 3 hrs after the dropwise addition was complete and pH was maintained at 11 with ammonium hydroxide throughout. After that the suspension was filtered and washed with demineralised water. Then it was dried at 110° C. overnight and calcined in air at 400° C for 1 hr. The sample was identified as a crystalline hydroxyapatite type by XRD analysis. Some amorphous material was found. TEM showed densely-packed short crystalline nano-rods <100 nm in length, and about 10 nm in diameter. The catalyst was tested as described in Example 1. The results are shown in Table 4.

The catalyst was tested as described in Example 1. The results are shown in Table 4.

TABLE 5

| Ex. | Catalyst composition | Contact time [s] | MMA + MAA yield [%] | MAA selectivity [%] | MMA + MAA selectivity [%] | DME [mole %] | DEK [mole %] | Toluene [mole %] |
|---|---|---|---|---|---|---|---|---|
| New Ex 13 | Sr-HAp pH11__1.67 | 5.2 | 7.0 | 0.7 | 85.9 | 0.04 | 0.0045 | 0.00005 |
| New Ex 14 | Sr-HAp pH11__1.50 | 5.2 | 6.8 | 0.8 | 92.0 | 0.17 | 0.0024 | 0.00010 |
| New Ex 15 | Sr-HAp pH11__1.00 | 5.0 | 5.6 | 1.2 | 94.1 | 0.21 | 0.0012 | 0.00006 |

Example 11

Preparative Example 11

23.6 g of calcium nitrate tetrahydrate $Ca(NO_3)_2 \cdot 4H_2O$ was dissolved in 100 ml of demineralised water and pH was adjusted to 5 with dilute aqueous nitric acid. 7.9 g of diammonium hydrogen phosphate $(NH_4)_2HPO_4$ in 50 ml of demineralised water at pH 5 was added dropwise to the solution of calcium nitrate at the temperature of 80° C. while stirring. A suspension forms on addition of the phosphate to the nitrate solution. This mother suspension was continuously stirred for 3 hrs after the dropwise addition was complete and pH was maintained at 5 with dilute aqueous nitric acid throughout. After that the suspension was filtered and washed with demineralised water. Then it was dried at 110° C. overnight and calcined in air at 400° C. for 1 hr. TEM showed large flat structures, blade or sheet-like, greater than 1 micron in 2 of their dimensions. The edges of the flat structures were fractured into parallel nano-rods of high aspect ratio:greater than 100 nm long, but less than 20 nm diameter. It was identified by XRD that the sample is a combination of monetite $CaHPO_4$ and pyrophosphate $Ca_2P_2O_7$ phases probably masking an underlying HAP phase. The catalyst was tested as described in Example 1. The results are shown in Table 4.

Example 12

Preparative Example 12

14.2 g of calcium nitrate tetrahydrate $Ca(NO_3)_2 \cdot 4H_2O$ was dissolved in 100 ml of demineralised water and pH was adjusted to 5 with dilute aqueous nitric acid. 7.9 g of diammonium hydrogen phosphate $(NH_4)_2HPO_4$ in 50 ml of demineralised water at pH 5 was added dropwise to the solution of calcium nitrate at the temperature of 80° C. while stirring. A suspension forms on addition of the phosphate to the nitrate solution. This mother suspension was continuously stirred for 3 hrs after the dropwise addition was complete and pH was maintained at 5 with dilute aqueous nitric acid throughout. After that the suspension was filtered and washed with demineralised water. Then it was dried at 110° C. overnight and calcined in air at 400° C. for 1 hr. TEM showed non-uniform particles, predominantly as sheets, but also as rods enmeshed in amorphous material. XRD identified the presence of pyrophosphate $Ca_2P_2O_7$. Amorphous material was also found.

Example 13

Preparative Example 13

21.2 g of strontium nitrate $Sr(NO_3)_2$ was dissolved in 100 ml of demineralised water and pH was adjusted to 11 with ammonium hydroxide. 7.9 g of diammonium hydrogen phosphate $(NH_4)_2HPO_4$ in 50 ml of demineralised water at pH 11 was added dropwise to the solution of strontium nitrate at the temperature of 80° C. while stirring. A suspension forms on addition of the phosphate to the nitrate solution. This mother suspension was continuously stirred for 3 hrs after the dropwise addition was complete and pH was maintained at 11 with ammonium hydroxide throughout. After that the suspension was filtered and washed with demineralised water.

Then it was dried at 110° C. overnight and calcined in air at 400° C. for 1 hr. The sample was identified as a crystalline strontium-apatite type by XRD analysis. TEM images show nano-rods as the only observed morphology, typically 100 nm length and 20 nm diameter. The catalyst was tested as described in Example 1. The results are shown in Table 5.

Example 14

Preparative Example 14

19.0 g of strontium nitrate $Sr(NO_3)_2$ was dissolved in 100 ml of demineralised water and pH was adjusted to 11 with ammonium hydroxide. 7.9 g of diammonium hydrogen phosphate $(NH_4)_2HPO_4$ in 50 ml of demineralised water at pH 11 was added dropwise to the solution of strontium nitrate at the temperature of 80° C. while stirring. A suspension forms on addition of the phosphate to the nitrate solution. This mother suspension was continuously stirred for 3 hrs after the dropwise addition was complete and pH was maintained at 11 with ammonium hydroxide throughout. After that the suspension was filtered and washed with demineralised water.

Then it was dried at 110° C. overnight and calcined in air at 400° C. for 1 hr. The sample was identified as a crystalline strontium-apatite type by XRD analysis. TEM images show tightly clustered nano-rods, typically 100 nm length and 20 nm diameter. The catalyst was tested as described in Example 1. The results are shown in Table 5.

Example 15

Preparative Example 15

12.7 g of strontium nitrate $Sr(NO_3)_2$ was dissolved in 100 ml of demineralised water and pH was adjusted to 11 with ammonium hydroxide. 7.9 g of diammonium hydrogen phosphate $(NH_4)_2HPO_4$ in 50 ml of demineralised water at pH 11 was added dropwise to the solution of strontium nitrate at the temperature of 80° C. while stirring. A suspension forms on addition of the phosphate to the nitrate solution. This mother suspension was continuously stirred for 3 hrs after the dropwise addition was complete and pH was maintained at 11 with ammonium hydroxide throughout. After that the suspension was filtered and washed with demineralised water.

Then it was dried at 110° C. overnight and calcined in air at 400° C. for 1 hr. The sample was identified as a strontium-apatite type by XRD analysis. TEM images show clusters of long nano-rods, typically 100-500 nm in length, and 10-20 nm in diameter. The catalyst was tested as described in Example 1. The results are shown in Table 5.

B Dimethoxymethane Feed

TABLE 6

| | Catalyst composition | Contact time [s] | MMA + MAA yield [%] | MAA selectivity [%] | MMA + MAA selectivity [%] | DME [mole %] | Water content [wt %] | DEK [mole %] | Toluene [mole %] |
|---|---|---|---|---|---|---|---|---|---|
| Ex 16 | Ca-HAp pH7_1.67 | 16.0 | 4.9 | 0.03 | 89.59 | 1.0 | 0.06 | 0.0095 | 0.00009 |
| Ex 17 | Ca-HAp pH11_1.67 | 14.9 | 6.2 | 1.7 | 81.9 | 0.6 | 0.09 | 0.0249 | 0.00018 |
| Comp Ex 5 | AlPO_TiO$_2$_B_urea | 14.3 | 4.9 | 3.7 | 57.8 | 11.4 | 2.21 | 0.0263 | 0.00388 |
| Comp Ex 6 | AlPO | 9.7 | 15.0 | 9.6 | 81.01 | 8.3 | 2.32 | 0.0107 | 0.00604 |
| Comp Ex 7 | AlPO_MgPO | 12.0 | 3.0 | 0.2 | 50.3 | 6.5 | 0.15 | 0.0104 | 0.00086 |
| Comp Ex 8 | TiO$_2$_Ca$_3$(PO$_4$)$_2$_B_urea | 9.4 | 3.2 | 0.1 | 58.3 | 0.8 | 0.05 | 0.0149 | 0.00046 |
| Comp Ex 9 | Comm Ca-HAp 289396 | 11.7 | 0.23 | 0.0 | 64.7 | 0.4 | 0.03 | 0.0033 | 0.00008 |
| Comp Ex 10 | Comm Ca-HAp 677418 | 10.3 | 0.008 | 0.8 | 1.36 | 0.006 | 0.05 | 0.1477 | 0.00000 |
| Comp Ex 11 | Comm Ca$_2$P$_2$O$_7$ 693871_1 | 10.5 | 0.095 | 2.6 | 29.0 | 2.5 | 0.03 | 0.0009 | 0.00017 |

Example 16

The catalyst was prepared as in preparative example 1. Catalyst testing: 3 g of catalyst was placed in a stainless steel tubular reactor connected to a vaporiser. The reactor was heated to 350° C. and vaporiser to 300° C. The mixture of 70 wt % of methyl propionate and 30 wt % of dimethoxymethane was passed through. The condensed reaction mixture was analysed by gas chromatography equipped with CP-Sil 1701.

Example 17

The catalyst was prepared as in preparative example 6. The catalyst was tested as described in example 16.

Comparative Example 5

The catalyst was prepared as in comparative preparative example 1.
The catalyst was tested as described in example 16.

Comparative Example 6

The catalyst was prepared as in comparative preparative example 2
The catalyst was tested as described in example 16.

Comparative Example 7

Comparative Preparative Example 7

3 g of magnesium phosphate hydrate Mg$_3$(PO$_4$)$_2$.xH$_2$O (Aldrich catalogue number 344702) was mixed with 3 g of aluminium phosphate (prepared as in comparative example 2). A paste was produced by addition of 5 ml of demineralised water. The paste was dried for 2 hrs at 120° C. and then heated for 4 hrs at 600° C.

The catalyst was tested as described in example 16.

Comparative Example 8

Comparative Preparative Example 8

The catalyst was synthesised following the preparation method disclosed in U.S. Pat. No. 4,118,588 patent in Example 3.

3 g of titanium dioxide TiO$_2$ (Aldrich catalogue number 634662), 2.3 g of calcium phosphate Ca$_3$(PO$_4$)$_2$ (Aldrich catalogue number 50552) and 0.75 g of boric acid H$_3$BO$_3$ were mixed together. A paste was produced by addition of 0.25 g of urea in 5 ml of demineralised water. The paste was dried for 12 hrs at 120° C. and then heated for 3 hrs at 580° C.

The catalyst was tested as described in example 16.

Comparative Example 9

Commercial Ca-hydroxyapatite was used from Aldrich with catalogue number of 289396.

The sample was confirmed as a crystalline hydroxyapatite type by XRD analysis. TEM showed the presence of agglomerated irregular sphere like particles.

Some amorphous material was found.

The catalyst was tested as described in example 16.

Comparative Example 10

Commercial Ca-hydroxyapatite was used from Aldrich with catalogue number of 677418.

BET surface area disclosed by Aldrich is 9.4 m$^2$/g.

The sample was confirmed as a crystalline hydroxyapatite type by XRD analysis. TEM analysis revealed sphere like crystals. Some amorphous material was found.

The catalyst was tested as described in example 16.

Comparative Example 11

Commercial $Ca_2P_2O_7$ was used from Aldrich with catalogue number of 693871.

BET surface area disclosed by Aldrich is 12 m$^2$/g. TEM showed sphere like non-crystalline particles.

The catalyst was tested as described in example 16. The results are shown in table 6.

TABLE 7

| Ex. | Catalyst composition | Contact time [s] | MMA + MAA yield [%] | MAA selectivity [%] | MMA + MAA selectivity [%] | DME [mole %] | Water content [wt %] | DEK [mole %] | Toluene [mole %] |
|---|---|---|---|---|---|---|---|---|---|
| Ex 18 | Ca-HAp pH7_1.5 | 10.5 | 5.9 | 0.02 | 89.29 | 2.5 | 0.03 | 0.0048 | 0.00025 |
| Ex 19 | Ca-HAp pH7_1 | 3.3 | 1.2 | 0.1 | 84.1 | 0.7 | 0.02 | 0.0050 | 0.00015 |

Example 18

The catalyst was prepared as in preparative Example 7.

The catalyst was tested as described in example 16 and the results are shown in table 7.

Example 19

The catalyst was prepared as in preparative Example 8.

The catalyst was tested as described in example 16 and the results are shown in table 7.

Example 20

The catalyst of preparative example 13 was tested as described in example 16. The results are shown in table 8.

Example 21

The catalyst of preparative example 14 was tested as described in example 16. The results are shown in table 8.

Example 22

The catalyst of preparative example 15 was tested as described in example 16. The results are shown in table 8.

TABLE 8

| Ex. | Catalyst composition | Contact time [s] | MMA + MAA yield [%] | MAA selectivity [%] | MMA + MAA selectivity [%] | DME [mole %] | Water content [wt %] | DEK [mole %] | Toluene [mole %] |
|---|---|---|---|---|---|---|---|---|---|
| Ex 20 | Sr-HAp pH11_1.67 | 11.6 | 4.1 | 0.03 | 73.3 | 0.07 | 0.04 | 0.0747 | 0.00012 |
| Ex 21 | Sr-HAp pH11_1.50 | 10.9 | 5.9 | 0.02 | 91.3 | 0.45 | 0.06 | 0.0030 | 0.00011 |
| Ex 22 | Sr-HAp pH11_1.00 | 12.4 | 8.7 | 0.02 | 92.4 | 0.66 | 0.11 | 0.0064 | 0.00008 |

Example 23

Preparative Example 23

21.2 g of strontium nitrate $Sr(NO_3)_2$ was dissolved in 100 ml of demineralised water and pH was adjusted to 7 with ammonium hydroxide. 7.9 g of diammonium hydrogen phosphate $(NH_4)_2HPO_4$ in 50 ml of demineralised water at pH 7 was added dropwise to a solution of strontium nitrate at the temperature of 80° C. while stirring. The mother suspension was mixed for 3 hrs and pH was maintained at 7 with ammonium hydroxide throughout. After that the suspension was filtered and washed with demineralised water.

Then it was dried at 110° C. overnight and calcined in air at 400° C. for 1 hr. The sample was identified as a crystalline strontium pyrophosphate by XRD analysis. TEM images show large flat structures, blade or sheet-like, typically 2-5 micron in length and 0.2-0.5 micron in width. The flat structures were fringed with clusters of nano-rod structures, with individual rods being typically 20 nm in diameter and 200 nm in length.

The catalyst was tested as described in example 1. The results are shown in Table 9.

Example 24

The catalyst of example 23 was tested with dimethoxymethane feed, as described in Example 16. The results are shown in Table 9.

TABLE 9

| Ex. | Catalyst composition | Contact time [s] | MMA + MAA yield [%] | MAA selectivity [%] | MMA + MAA selectivity [%] | DME [mole %] | Water content [wt %] | DEK [mole %] | Toluene [mole %] |
|---|---|---|---|---|---|---|---|---|---|
| Ex. 23 | Sr2P2O7 pH7_1.67 | 11.3 | 4.5 | 0.6 | 94.1 | 0.2 | — | 0.0011 | 0.00014 |
| Ex. 24 | Sr2P2O7 pH7_1.67 | 11.1 | 2.5 | 0.05 | 88 | 0.4 | 0.03 | 0.0058 | 0.00009 |

Table 10 shows the Ca:P synthesis ratios of various examples and comparative examples as well as the Ca:P ratios in the final crystals (XRF) and on the crystal surfaces (XPS). Comparative example 12 is a commercial pyrophosphate in the form of amorphous spheres purchased from Aldrich under catalogue number 693871. It can be seen that at the ideal hydroxyapatite ratio of 1.67 both the bulk crystal and the crystal surface are depleted in calcium but that the surface is more depleted. However, at low M:P synthesis ratios ideal for pyrophosphates of 1:1, the surface is richer in metal than the bulk of the crystal. This suggests the formation of a preferred surface arrangement on the crystals. The surface and bulk ratios for a series of examples are plotted in FIG. 1. It can be seen that at higher overall ratios the surface ratio is depressed and that at lower overall ratios the surface ratio is increased.

Figure 7:
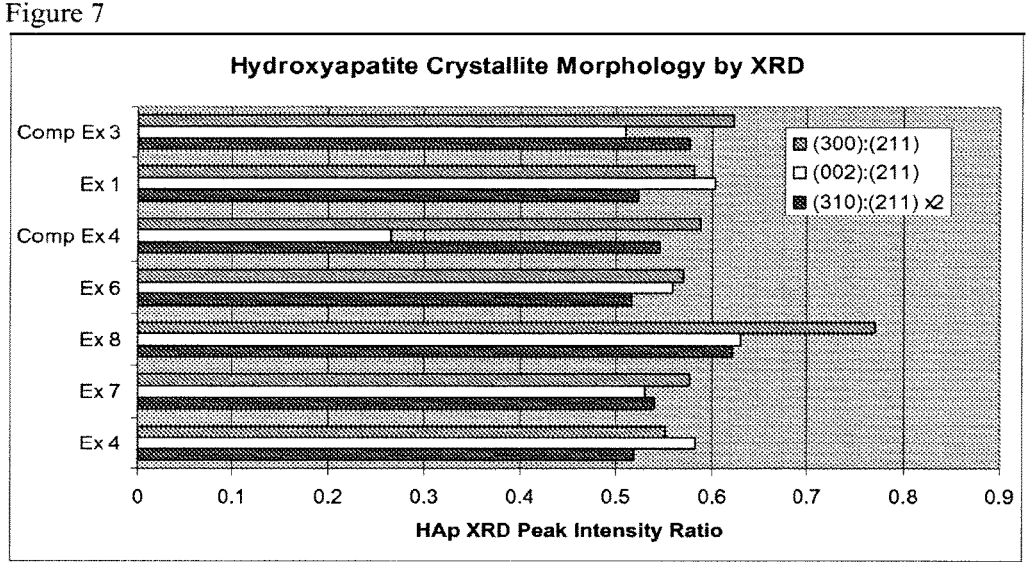
FIG. 7 compares crystallite morphology by XRD for several examples and comparative examples.

The XRD peak intensity data was collected and the ratios of certain peaks for several samples were compared. The results are shown in FIG. 7. The 002:211 ratio for the samples of the invention could be indicative of a strong nano-rod presence.

TABLE 10

| Example | Ca:P (stoich) | XRF Peak Area Ratio (Ca:P) | Bulk Ca:P (XRF m/m) | Surface Ca:P (XPS m/m) |
|---|---|---|---|---|
| Comp Ex 12 | 1.00 | 2.505 | 0.940 | 0.89 |
| Comp Ex 3 | 1.67 | 4.046 | 1.597 | 1.42 |
| Comp ex 4 | 1.67 | 4.748 | 1.896 | 1.78 |
| Ex 3 | 1.67 | 2.711 | 1.028 | 1.08 |
| Ex 6 | 1.67 | 4.086 | 1.614 | 1.49 |
| Ex 1 | 1.67 | 4.168 | 1.648 | 1.46 |
| Ex 8 | 1.00 | 3.531 | 1.377 | 1.31 |
| Ex 7 | 1.50 | 3.846 | 1.511 | 1.38 |
| Ex 9 | 1.67 | 3.801 | 1.492 | 1.36 |
| Ex 11 | 1.67 | 2.945 | 1.128 | 1.23 |

What is claimed is:

1. A catalyst system for the reaction of formaldehyde or a suitable source thereof with a carboxylic acid or ester comprising a crystalline metal phosphate catalyst and a catalyst support wherein the metal phosphate has rod/needle like morphology.

2. The catalyst system according to claim 1, wherein the phosphate is selected from the group consisting of pyrophosphate, hydroxyphosphate, $PO_4^{3-}$ phosphate and mixtures thereof.

3. The catalyst system according to claim 2, wherein the phosphate is selected from the group consisting of pyrophosphate, hydroxyapatite, and mixtures thereof.

4. The catalyst system according to claim 1, wherein the phosphate is selected from the group consisting of Ca, Sr or Ba or mixtures thereof.

5. The catalyst system according to claim 1, wherein the catalysts are selected from the group consisting of strontium hydroxyapatite and calcium hydroxyapatite.

6. The catalyst system according to claim 1, wherein the catalyst is at least 50% w/w metal phosphate.

7. The catalyst system according to claim 1, wherein the catalyst has a surface layer of crystals depleted below a metal:phosphorus (M:P) mole ratio of 1.67.

8. The catalyst system according to claim 7, wherein the crystal surface metal:phosphorus (M:P) mole ratio is between 1.30 and 1.55.

9. The catalyst system according to claim 1, wherein doping elements are present in the catalyst at a level of up to 20 mol % of the metal M.

10. The catalyst system according to claim 9, wherein the doping elements are metal cations selected from the group consisting of Cs, K, Rb, Na, Li, Zn, Ti, Si, La, Ce, Eu, Mg if not used as a group II metal, Ba if not used as a group II metal, Pb, Cd, Ag, Co, Cu, Ni and Zr.

11. The catalyst system according to claim 1, wherein doping anions are present in the catalyst at a level of up to 20 mol % phosphate.

12. The catalyst system according to claim 11, wherein the doping anions are selected from the group consisting of carbonate, chloride and fluoride.

13. The catalyst system according to claim 1, wherein the catalyst is on a support selected from the group consisting of alumina, silica, silicon nitride, silicon carbide, colloidal silica, titania or aluminium phosphate.

14. The catalyst system according to claim 1, wherein the metal:phosphorus (M:P) mole ratio is between 0.8-1.8.

* * * * *